(12) United States Patent
Garza et al.

(10) Patent No.: US 12,403,231 B2
(45) Date of Patent: Sep. 2, 2025

(54) SMART DIALYSIS BAG DETECTION SYSTEM

(71) Applicant: Fresenius Medical Care Holdings, Inc., Waltham, MA (US)

(72) Inventors: Hernando Garrido Garza, Concord, CA (US); Gilberto Romero Saldivar, Lausanne (CH); Kulwinder Plahey, Martinez, CA (US); Irving Uziel Hernandez, Hidalgo, TX (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 18/242,279

(22) Filed: Sep. 5, 2023

(65) Prior Publication Data

US 2023/0405197 A1    Dec. 21, 2023

Related U.S. Application Data

(63) Continuation of application No. 17/066,436, filed on Oct. 8, 2020, now abandoned.

(51) Int. Cl.
*A61M 1/28* (2006.01)
*A61M 1/14* (2006.01)
(Continued)

(52) U.S. Cl.
CPC ............ *A61M 1/28* (2013.01); *A61M 1/1522* (2022.05); *A61M 1/1524* (2022.05);
(Continued)

(58) Field of Classification Search
CPC ........ A61M 1/15; A61M 1/154; A61M 1/159; A61M 1/28; A61M 1/281; A61M 1/282;
(Continued)

(56) References Cited

U.S. PATENT DOCUMENTS

2008/0253427 A1    10/2008   Kamen et al.
2009/0009290 A1    1/2009    Kneip et al.
(Continued)

FOREIGN PATENT DOCUMENTS

EP    3 561 551 A1    10/2019
EP    3 620 191 A1    3/2020
(Continued)

OTHER PUBLICATIONS

ISO 8637-1:2017 "Extracorporeal systems for blood purification—Part 1: Haemodialysers, haemodiafilters, haemofilters and haemoconcentrators," (Nov. 2017).
(Continued)

*Primary Examiner* — Kami A Bosworth
(74) *Attorney, Agent, or Firm* — Leydig, Voit & Mayer, Ltd.

(57) ABSTRACT

A dialysis machine (e.g., a peritoneal dialysis (PD) machine) can include a safety feature that enables the dialysis machine to automatically identify the connections made by a user in preparation for treatment. A smart connector is disclosed that uses a split RFID device that is operational when a first portion of the connector is mated to a second portion of the connector, and is not operational when the first portion is disconnected from the second portion. In an embodiment, the split RFID device incorporates an RFID chip in the first portion of the connector and an antenna in the second portion of the connector. In an embodiment, the RFID chip can store a tag that encodes information that indicates a formulation or a volume of a dialysis bag connected to the ports of a disposable cassette such that the dialysis machine can automatically discover the configuration of the dialysis setup.

13 Claims, 16 Drawing Sheets

(51) Int. Cl.
   *A61M 1/16* (2006.01)
   *A61M 39/10* (2006.01)

(52) U.S. Cl.
   CPC ............ *A61M 1/154* (2022.05); *A61M 1/155* (2022.05); *A61M 1/1561* (2022.05); *A61M 1/159* (2022.05); *A61M 1/1601* (2014.02); *A61M 1/1621* (2014.02); *A61M 39/10* (2013.01); *A61M 2205/12* (2013.01); *A61M 2205/3379* (2013.01); *A61M 2205/3553* (2013.01); *A61M 2205/3592* (2013.01); *A61M 2205/52* (2013.01); *A61M 2205/60* (2013.01)

(58) Field of Classification Search
   CPC .... A61M 1/284; A61M 1/287; A61M 5/1407; A61M 5/16827; A61M 39/10; A61M 2039/1022; A61M 2205/3569; A61M 2205/3592; A61M 2205/60; A61M 2205/6018; A61M 2205/6027
   See application file for complete search history.

(56) References Cited

U.S. PATENT DOCUMENTS

| | | |
|---|---|---|
| 2009/0012448 A1 | 1/2009 | Childers et al. |
| 2009/0118594 A1 | 5/2009 | Zdeblick |
| 2009/0275881 A1 | 11/2009 | Lo et al. |
| 2009/0299272 A1 | 12/2009 | Hopping et al. |
| 2010/0312174 A1 | 12/2010 | Hoffman |
| 2011/0092893 A1 | 4/2011 | Demers et al. |
| 2011/0106002 A1 | 5/2011 | Helmore et al. |
| 2011/0186517 A1 | 8/2011 | Hedmann et al. |
| 2011/0196279 A1 | 8/2011 | Maierhofer et al. |
| 2012/0229272 A1 | 9/2012 | Jacob et al. |
| 2014/0364800 A1 | 12/2014 | McGill et al. |
| 2015/0238673 A1 | 8/2015 | Gerber et al. |
| 2017/0239404 A1 | 8/2017 | Shavit |
| 2017/0266429 A1 | 9/2017 | Striggow et al. |
| 2019/0224352 A1 | 7/2019 | Rasooly et al. |
| 2021/0299376 A1 | 9/2021 | Gleim et al. |

FOREIGN PATENT DOCUMENTS

| | | |
|---|---|---|
| MX | 359180 B | 9/2018 |
| WO | 2009/094183 A1 | 7/2009 |
| WO | 2018/071651 A1 | 4/2018 |

OTHER PUBLICATIONS

ISO 80369-7:2016 "Small-bore connectors for liquids and gases in healthcare applications—Part 7: Connectors for intravascular or hypodermic applications," (Dec. 1, 2016).

U.S. Appl. No. 17/066,436, filed Oct. 8, 2020.

SMART DIALYSIS BAG DETECTION SYSTEM

CROSS-REFERENCE TO RELATED APPLICATIONS

This application is a continuation of U.S. application Ser. No. 17/066,436, filed on Oct. 8, 2020, which is incorporated by reference herein in its entirety.

BACKGROUND

Dialysis is a treatment used to support a patient with insufficient renal function. The two principal treatment options are hemodialysis (HD) and peritoneal dialysis (PD). During hemodialysis, the patient's blood is removed, e.g., via an arteriovenous (AV) fistula or other methods (e.g., AV graft), and passed through a dialyzer of a dialysis machine while also passing a dialysis solution, referred to as dialysate, through the dialyzer. A semi-permeable membrane in the dialyzer separates the blood from the dialysate within the dialyzer and facilitates the exchange of waste products (e.g., urea, creatine, potassium, etc.) between the blood stream and the dialysate. The membrane prevents the transfer of blood cells, protein, and other important components in the blood stream from entering the dialysate solution. The cleaned blood stream is then returned to the patient's body. In this way, the dialysis machine functions as an artificial kidney for cleaning the blood in patients with insufficient renal function.

In contrast with hemodialysis, the peritoneal dialysis treatment option introduces dialysate into a patient's peritoneal cavity, which is an area in the abdomen between the parietal peritoneum and visceral peritoneum (e.g., a space between the membrane that surrounds the abdominal wall and the membranes that surround the internal organs in the abdomen). The lining of the patient's peritoneum functions as a semi-permeable membrane that facilitates the exchange of waste product between the bloodstream and the dialysate, similar in function to the membrane in the dialyzer of the hemodialysis machine. The patient's peritoneal cavity is drained and filled with new dialysate over a number of PD cycles. Peritoneal dialysis can be performed using either gravity or an automated pumping mechanism to fill and drain the abdomen during a PD cycle.

Automated PD machines, sometimes referred to as PD cyclers, are designed to control the PD treatment process so that it can be performed at home without clinical staff, typically while the patient sleeps overnight so as to minimize interference with the patient's life. The process is referred to as continuous cycler-assisted peritoneal dialysis (CCPD). Many PD cyclers are designed to automatically infuse, dwell, and drain dialysate to and from the peritoneal cavity. The PD treatment typically lasts several hours, often beginning with an initial drain phase to empty the peritoneal cavity of used or spent dialysate that was left in the peritoneal cavity at the end of the last PD treatment. The sequence then proceeds through a progression of fill, dwell, and drain phases that follow sequentially. A group of fill, dwell, and drain phases, in order, can be referred to as a PD cycle.

Sterile dialysate solution is provided to the patient or caregiver in a variety of volumes and compositions. For example, dialysate bags may commonly be provided in 2 liter (L), 3 L, or 5 L volumes. Dialysate solution can also be provided in a 1.5% dextrose concentration, a 2.5% dextrose concentration, a 4.25% dextrose concentration, or the like. Furthermore, the solution can include various concentrations of other elements such as magnesium and/or calcium.

Conventional PD machines typically rely on the patient or caregiver to connect the bags to the PD machine or disposable cassette. The cassette can include a number of lines including a plurality of lines connected to one or more dialysate bags, a heater line bag, a patient line, and a drain line. The PD machine may have limited capability to confirm that a patient has connected a dialysate bag to the correct line (such as by monitoring a line pressure of each line), but cannot confirm that the patient or caregiver has connected a dialysate bag with the correct volume or concentration to said line. Incorrect connections can cause interruptions in treatment (e.g., where a patient is prompted to replace the dialysate bag) or could be dangerous to the patient (e.g., could cause electrolyte imbalance, hypervolemia, or underdialysis). Thus, there is a desire to implement new safety mechanisms that enable the PD machine to verify the source of dialysate introduced to each line attached to the PD machine.

SUMMARY

In accordance with one aspect of the disclosure, a dialysis system is provided that includes a safety feature. The safety feature enables the dialysis system to monitor the formulation and volume of one or more dialysate bags connected to the dialysis system. Each dialysate bag is connected to a fluid line with one half of a connector attached thereto. The other half of the connector is attached to another fluid line connected to the dialysis system or a port of a disposable cassette used by a peritoneal dialysis machine. When the first half of the connector is connected to the second half of the connector, fluidly coupling the dialysate bag to the dialysis system, a wireless device in the connector is enabled, which can then be read by the dialysis machine to identify the type of dialysate (e.g., the formulation) and a volume of the dialysate connected to the dialysis system.

In an embodiment, the dialysis system includes a wireless interface in communication with one or more connectors attached to fluid lines, and a reader configured to access information stored in the one or more connectors. Each connector of the one or more connectors includes a first portion and a second portion. At least one of the first portion or the second portion includes a radio frequency identifier (RFID) device that is operational when the first portion is mated with the second portion and is not operational when the first portion is disconnected from the second portion.

In some embodiments, the reader is a near field communication (NFC) device. The NFC device is configured to: transmit a radio frequency (RF) signal over the wireless interface, and receive an RFID signal from a first connector of the one or more connectors that includes a tag that indicates at least one of a formulation or a volume of a dialysis bag connected to a first fluid line fluidly coupled to the first connector.

In some embodiments, the dialysis system further includes a disposable cassette that includes a plurality of ports, each port fluidly coupled to the second portion of a corresponding connector of the one or more connectors.

In an embodiment, the second portion includes an antenna of the RFID device and the first portion of the corresponding connector, when mated to the second portion, includes an RFID chip. In another embodiment, the second portion includes an interconnect configured to route a signal from a first terminal to a second terminal. The first portion of the corresponding connector, when mated to the second portion, includes an RFID chip and an antenna, and a signal interconnect from the RFID chip is connected to the first terminal and the second terminal is connected to the antenna.

In yet other embodiments, the second portion includes a memory that stores second information that identifies the port of the disposable cassette fluidly connected to the corresponding connector. The first portion of the corresponding connector, when mated to the second portion, includes an RFID chip or a memory that stores first information that indicates at least one of a formulation or a volume of a dialysis bag, and wherein the RFID chip is configured to encode the first information and the second information to generate a tag that is transmitted to the reader.

In some embodiments, the second portion comprises a female connector that includes a tapered orifice. The first portion comprises a male connector that includes a protrusion that fits in the tapered orifice. The at least one component of the RFID device is encapsulated in the first portion in accordance with an overmolding manufacturing process.

In accordance with a second aspect of the present disclosure, a smart connector for a medical device is disclosed. The smart connector includes a first portion that includes a radio frequency identifier (RFID) chip, and a second portion that enables operation of the RFID chip when mated to the first portion and disables operation of the RFID chip when disconnected from the first portion.

In some embodiments, the second portion includes an antenna. A radio frequency (RF) signal received by the antenna causes the RFID chip to transmit, via the antenna, an RFID signal that includes a tag. The tag comprises one or more bits that encode information corresponding to at least one of a formulation or a volume of a dialysis bag connected to the first portion of the smart connector.

In some embodiments, the first portion is a male connector and the second portion is a female connector that includes a tapered orifice.

In some embodiments, the first portion further includes an antenna, and wherein an RFID signal generated by the RFID chip is routed through the second portion to the antenna.

In some embodiments, the second portion includes a memory that stores second information that identifies a port of a disposable cassette. The first portion includes the RFID chip or a memory that stores first information that indicates at least one of a formulation or a volume of a dialysis bag, and wherein the RFID chip is configured to encode the first information and the second information to generate a tag.

In accordance with a third aspect of the present disclosure, a method for operating a dialysis machine is disclosed. The method includes the steps of: transmitting, via a wireless interface, a radio frequency (RF) signal, and receiving, via the wireless interface, at least one tag corresponding to one or more connectors attached to fluid lines. Each connector of the one or more connectors includes a first portion and a second portion, and at least one of the first portion or the second portion includes a radio frequency identifier (RFID) device that is operational when the first portion is mated with the second portion and is not operational when the first portion is disconnected from the second portion.

In some embodiments, an RFID signal from a first connector of the one or more connectors includes a tag that indicates at least one of a formulation or a volume of a dialysis bag connected to a first fluid line fluidly coupled with the first connector.

In some embodiments, the steps further include: receiving prescription information related to treatment of a patient of the dialysis machine; comparing information received from at least one connector of the one or more connectors to the prescription information to determine whether at least one of formulation or volume of one or more dialysis bags connected to the one or more connectors matches the prescription information; and initiating a dialysis treatment when the information matches the prescription information, or setting an alarm when the information does not match the prescription information.

In some embodiments, the steps further include prompting a user to connect fluid lines to a disposable cassette, and transmitting, periodically, a radio frequency (RF) signal via a wireless interface to poll the one or more connectors to receive tags that indicate when a first portion of each connector of the one or more connectors is mated to a second portion of the connector.

In some embodiments, a near field communication (NFC) device receives the at least one tag from the wireless interface and is configured to: compare the at least one tag to a history of stored tags to determine if any of the tags in the at least one tag represent newly discovered connections.

In accordance with another aspect of the disclosure, a non-transitory computer readable storage medium is provided. The computer readable storage medium stores instructions that, when executed by a processor, causes a dialysis machine to perform steps of the method set forth above.

DETAILED DESCRIPTION

Figure 1:
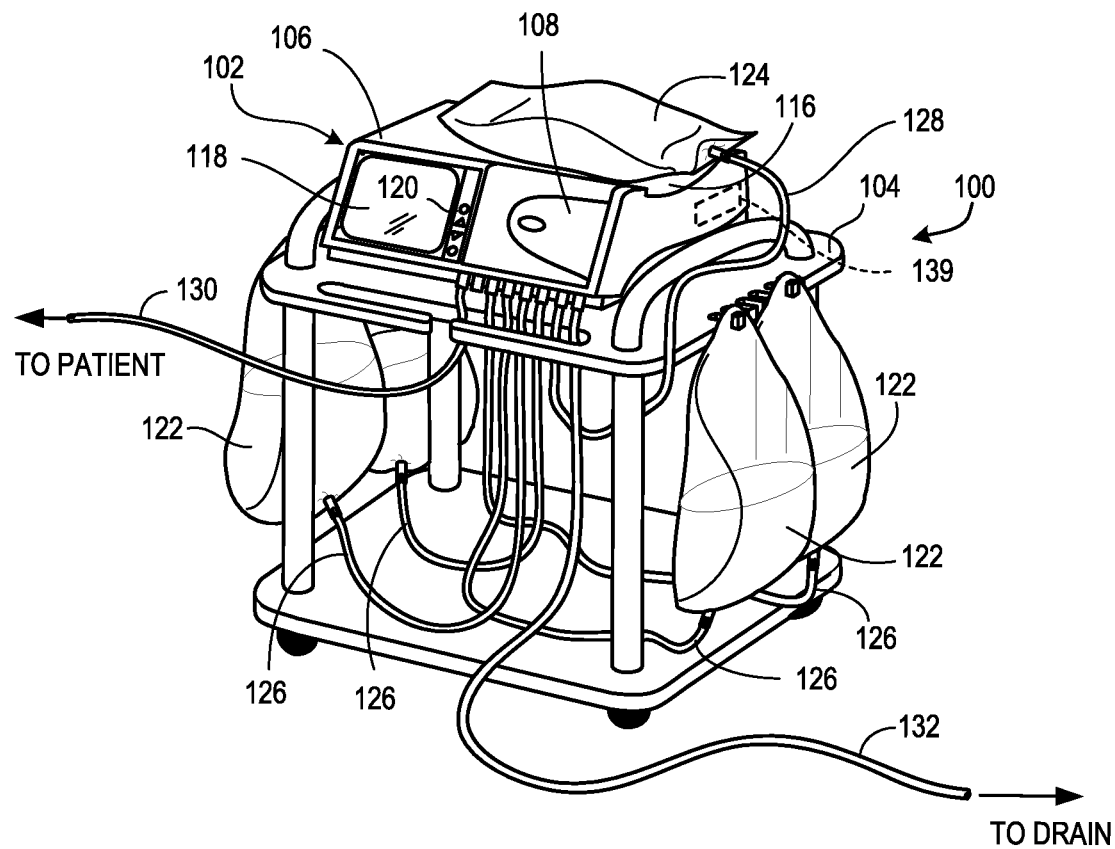
FIG. 1 illustrates a peritoneal dialysis (PD) system, in accordance with some embodiments.

A dialysis machine, such as a peritoneal dialysis (PD) machine, can be designed to include a safety feature. The safety feature enables the dialysis machine to detect the formulation and/or volume of dialysate bags connected to the dialysis machine automatically. In some embodiments, each fluid connector attached to a disposable cassette of a PD machine includes a radio frequency identifier (RFID) device that can be accessed wirelessly by a reader included in the PD machine. The RFID device is configured such that the circuit and/or components of the RFID device are split between the male and female connectors of the fluid connector. For example, the female connector attached to the disposable cassette can include an antenna portion of the RFID device and the male connector attached to the dialysate bag can include a chip portion of the RFID device. The chip portion includes information (e.g., a tag) that can be decoded by the dialysis machine to identify the formulation and/or volume of the dialysate bag.

In some embodiments, the female connector attached to the dialysate bag can include a memory that stores the information that identifies the formulation and/or volume of the dialysate bag, and the male connector attached to the disposable cassette can include the chip portion and the antenna portion of the RFID device. The circuit of the RFID device is designed in such a manner as to require the chip portion to be connected to the memory in the female connector in order to function as an RFID device.

In other embodiments, the female connector attached to the dialysate bag can include the chip portion and the antenna portion of the RFID device as well as a memory that stores the information that identifies the formulation and/or volume of the dialysate bag. The male connector attached to the disposable cassette can also include a memory that stores information that identifies the port of the disposable cassette, where the information can be combined by the chip portion to generate aggregate information that identifies both the formulation and/or volume of the dialysate bag and the particular port of the disposable cassette connected to the dialysate bag. It will be appreciated that any manner of splitting the RFID device between the male and female connectors such that operation of the RFID device is only enabled when the connection is made, and storing information that identifies the formulation and/or volume of the dialysate bag on the connector attached to the dialysate bag, is within the scope of the present disclosure. It will also be appreciated that, in some embodiments, the female connector can be attached to the disposable cassette and the male connector can be attached to the dialysate bag. In such embodiments, the components in each of the connectors can be swapped, compared to the embodiments described above.

In some embodiments, the information read from the tag(s) by the reader can be utilized by a controller of the dialysis machine to change the operation of the dialysis machine. For example, by automatically detecting the volume and/or concentration of the dialysate bag connected to each port of the disposable cassette, the dialysis machine can determine when a dialysis bag has been drained and switch to a new port to supply a heater bag with clean dialysate solution. As another example, different volumes of dialysate from two different dialysate bags with different concentrations of minerals or electrolytes can be mixed to create concentrations between the two source concentrations (e.g., equal volume of 1.5% dextrose and 2.5% dextrose solutions can be mixed to create a 2.0% dextrose solution, or a 10% dextrose solution can be mixed with pure saline to produce a concentration between 0-10%).

In an embodiment, the dialysis machine can set an alarm or alert the patient or caregiver of an issue detected during setup of the machine. For example, the dialysis machine can detect that a dialysis bag is connected to the wrong port of the disposable cassette and then alert the patient or caregiver of the mistake. In some embodiments, prescription data related to a treatment plan for a patient can be downloaded into the dialysis machine. The prescription data can include, e.g., a concentration of the dialysate solution as well as timing for each PD treatment cycle and a total number of cycles. The dialysis machine can confirm that the dialysate bags attached to the disposable cassette match the prescription information. In another example, given that the dialysis machine can read the expected volume of a dialysate bag, any discrepancy between the volume drawn from the dialysate bag and the expected volume can trigger an alarm that indicates that there could be a leak in the system, flow sensors could be malfunctioning, or the like.

FIG. 1 illustrates a peritoneal dialysis (PD) system 100, in accordance with some embodiments. The PD system 100 can include a PD machine 102, which can alternately be referred to as a PD cycler, seated on a cart 104. The PD machine 102 includes a housing 106, a door 108, and a cassette interface 110 that contacts a disposable PD cassette 112 when the cassette 112 is disposed within a cassette compartment 114 formed between the cassette interface 110 and the closed door 108. The cassette compartment 114, cassette interface 110, and cassette 112 are shown in more detail in FIG. 2. A heater tray 116 is positioned on top of the housing 106. The heater tray 116 is sized and shaped to accommodate a bag of PD solution such as dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bags 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The catheter may be surgically implanted in the patient and connected to the patient line 130 via a port, such as a fitting, prior to the PD treatment. The drain line 132 can be connected to a drain or drain receptacle and can be used to pass dialysate from the cassette 112 to the drain or drain receptacle during use.

The PD machine 102 also includes a control unit 139 (e.g., a processor, controller, system-on-chip (SoC), or the like). The control unit 139 can receive signals from and transmit signals to the touch screen display 118, the control panel 120, and the various other components of the PD system 100. The control unit 139 can control the operating parameters of the PD machine 102. In some embodiments, the control unit 139 includes an MPC823 PowerPC device manufactured by Motorola, Inc. As further discussed in detail elsewhere herein, in some embodiments, the control unit 139 may be configured to control disengaging and/or bypassing of a pump in connection with naturally draining the dialysate from a patient during the drain phase of a PD cycle.

Figure 2:
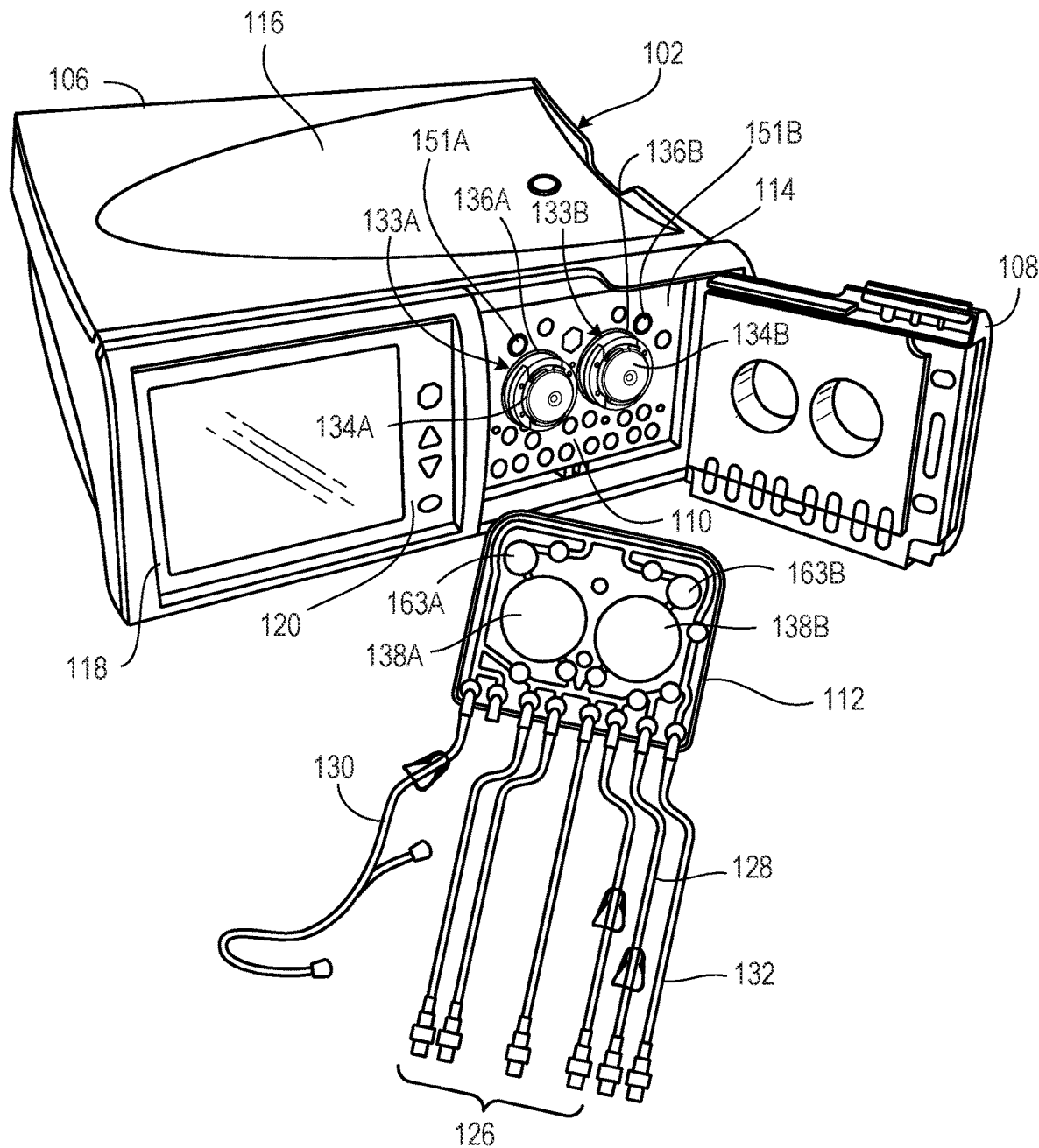
FIG. 2 is a perspective view of the PD machine and the PD cassette of the PD system of FIG. 1, in accordance with some embodiments

FIG. 2 is a perspective view of the PD machine 102 and the PD cassette 112 of the PD system 100 of FIG. 1, in accordance with some embodiments. As depicted in FIG. 2, the PD cassette 112 is placed proximate the cassette interface 110. The cassette 112 contains pump chambers 138A, 138B, pressure sensing chambers 163A, 163B, and valve chambers for controlling the flow of fluid through the cavities of the cassette 112. The cassette 112 is connected to the dialysate bag lines 126, the heater bag line 128, the patient line 130, and the drain line 132.

The cassette interface 110 includes a surface having holes formed therein. The PD machine 102 includes pistons 133A, 133B with piston heads 134A, 134B attached to piston shafts. The piston shafts can be actuated to move the piston heads 133A, 133B axially within piston access ports 136A, 136B formed in the cassette interface 110. The pistons 133A, 133B are sometimes referred to herein as pumps. In some embodiments, the piston shafts can be connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward on the lead screws. The stepper motors can be controlled by driver modules. The nuts, in turn, are connected to the piston shafts, which cause the piston heads 134A, 134B to move axially inward and outward as the stepper motors drive the lead screws. Stepper motor controllers provide the necessary current to be driven through the windings of the stepper motors to move the pistons 133A, 133B. The polarity of the current determines whether the pistons 133A, 133B are advanced or retracted. In some embodiments, the stepper motors require 200 steps to make a full rotation, and this corresponds to 0.048 inches of linear travel of the piston heads 134A, 134B.

In some embodiments, the PD system 100 also includes encoders (e.g., optical quadrature encoders) that measure the rotational movement and direction of the lead screws. The axial positions of the pistons 133A, 133B can be determined based on the rotational movement of the lead screws, as indicated by feedback signals from the encoders. Thus, measurements of the position calculated based on the feedback signals can be used to track the position of the piston heads 134A, 134B of the pistons 133A, 133B.

When the cassette 112 is positioned within the cassette compartment 114 of the PD machine 102 with the door 108 closed, the piston heads 134A, 134B of the PD machine 102 align with the pump chambers 138A, 138B of the cassette 112 such that the piston heads 134A, 134B can be mechanically connected to dome-shaped fastening members of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B. Retraction of the piston heads 134A, 134B away from the cassette 112 can increase the volume of the pump chambers 138A, 138B and cause dialysate to be drawn into the pump chambers 138A, 138B.

The cassette 112 also includes pressure sensor chambers 163A, 163B. When the cassette 112 is positioned within the cassette compartment 114 of the PD machine 102 with the door 108 closed, pressure sensors 151A, 151B align with the pressure sensor chambers 163A, 163B. Portions of a membrane that overlies the pressure sensor chambers 163A, 163B adhere to the pressure sensors 151A, 151B using vacuum pressure. Specifically, clearance around the pressure sensors 151A, 151B communicates vacuum to the portions of the cassette membrane overlying the pressure sensing chambers 163A, 163B to hold those portions of the cassette membrane tightly against the pressure sensors 151A, 151B. The pressure of fluid within the pressure sensing chambers 163A, 163B causes the portions of the cassette membrane overlying the pressure sensor chambers 163A, 163B to contact and apply a force to the pressure sensors 151A, 151B.

The pressure sensors 151A, 151B can be any sensors that are capable of measuring the fluid pressure in the pressure sensor chambers 163A, 163B. In some embodiments, the pressure sensors are solid state silicon diaphragm infusion pump force/pressure transducers. One example of such a sensor is the model 1865 force/pressure transducer manufactured by Sensym® Foxboro ICT. In some embodiments, the force/pressure transducer is modified to provide increased voltage output. The force/pressure transducer can, for example, be modified to produce an output signal of 0 to 5 volts.

Figure 3:
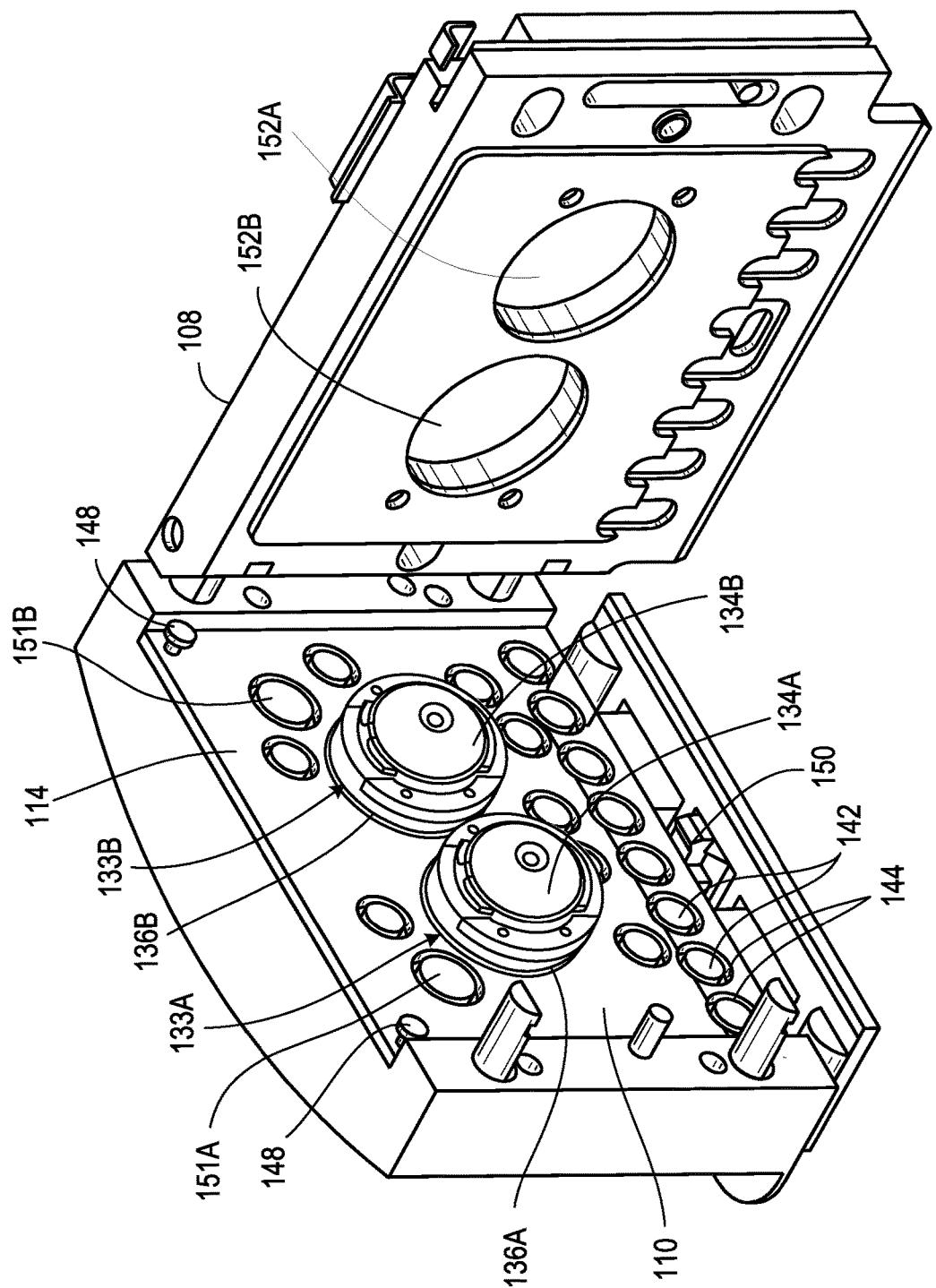
FIG. 3 is a perspective view of an open cassette compartment of the PD machine of FIG. 1, in accordance with some embodiments.

FIG. 3 is a perspective view of an open cassette compartment 114 of the PD machine 102 of FIG. 1, in accordance with some embodiments. As discussed above, the PD machine 102 includes pistons 133A, 133B disposed in piston access ports 136A, 136B, respectively. The PD machine 102 also includes multiple inflatable members 142 positioned within inflatable member ports 144 in the cassette interface 110. The inflatable members 142 align with depressible dome regions of the cassette 112 when the cassette 112 is positioned within the cassette compartment 114 of the PD machine 102. While only a couple of the inflatable members 142 are labeled in FIG. 3, it should be understood that the PD machine 102 includes an inflatable member 142 associated with each of the depressible dome regions of the cassette 112. The inflatable members 142 act, in cooperation with the depressible dome regions, as valves to direct dialysate through the cassette 112 in a desired manner during use. In particular, the inflatable members 142 bulge outward beyond the surface of the cassette interface 110 and into contact with the depressible dome regions of the cassette 112 when inflated, and retract into the inflatable member ports 144 and out of contact with the cassette 112 when deflated. By inflating certain inflatable members 142 to depress their associated dome regions on the cassette 112, certain fluid flow paths within the cassette 112 can be occluded. Thus, dialysate can be pumped through the cassette 112 by actuating the piston heads 134A, 134B, and can be guided along desired flow paths within the cassette 112 by selectively inflating and deflating the various inflatable members 142.

In some embodiments, locating pins 148 extend from the cassette interface 110 of the PD machine 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD machine 102 defines cylindrical recesses 152A, 152B that substantially align with the pistons 133A, 133B when the door 108 is in the closed position. When the cassette 112 is positioned within the cassette compartment 114 with the door 108 closed, the pump chambers 138A, 138B at least partially fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the surface of the pump chambers 138A, 138B, and the other portions of the door 108 support the other regions or surfaces of the cassette 112. The door 108 can counteract the forces applied by the inflatable members 142 and, therefore, allows the inflatable members 142 to actuate the depressible dome regions on the cassette 112. The engagement between the door 108 and the cassette 112 can also help to hold the cassette 112 in a desired position within the cassette compartment 114 to further ensure that the pistons 133A, 133B align with the fluid pump chambers 138A, 138B of the cassette 112.

The control unit 139 of FIG. 1 is connected to the pressure sensors 151A, 151B, to the stepper motors (e.g., the drivers for the stepper motors) that drive the pistons 133A, 133B, and to the encoders that monitor rotation of the lead screws attached to the stepper motors such that the control unit 139 can receive signals from and transmit signals to those components of the PD system 100. The control unit 139 monitors the components to which it is connected to determine whether any complications exist within the PD system 100, such as the presence of an occlusion or blockage in the patient line 130.

Figure 4:
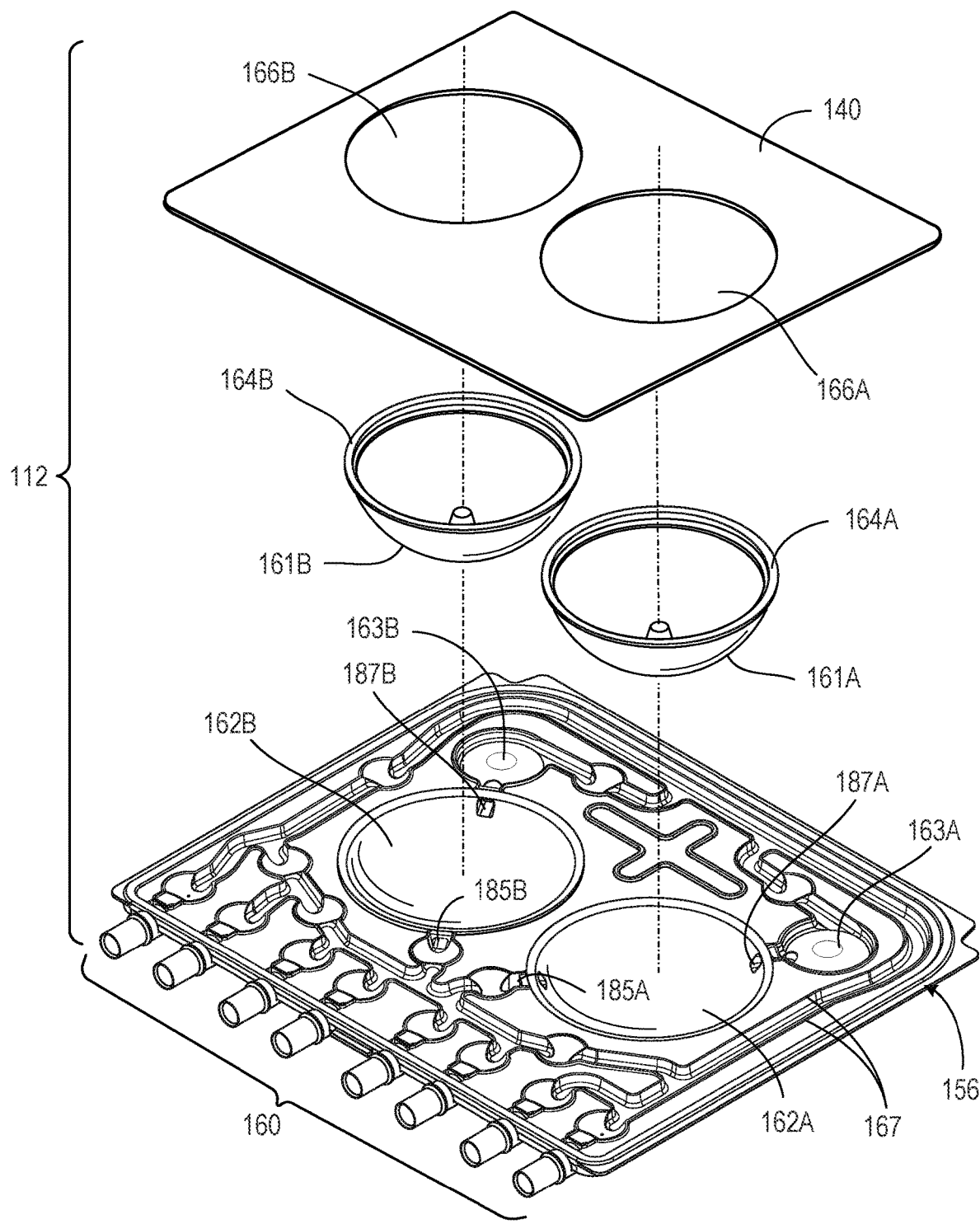
FIG. 4 is an exploded, perspective view of the PD cassette of FIG. 2, in accordance with some embodiments.
Figure 5:
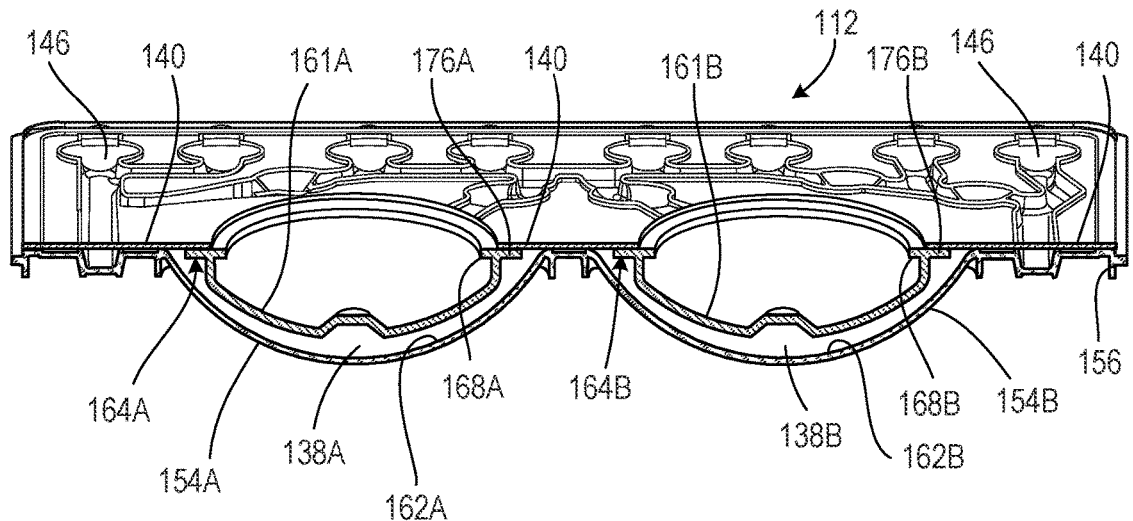
FIG. 5 is a cross-sectional view of the fully assembled PD cassette of FIG. 2, in accordance with some embodiments.
Figure 6:
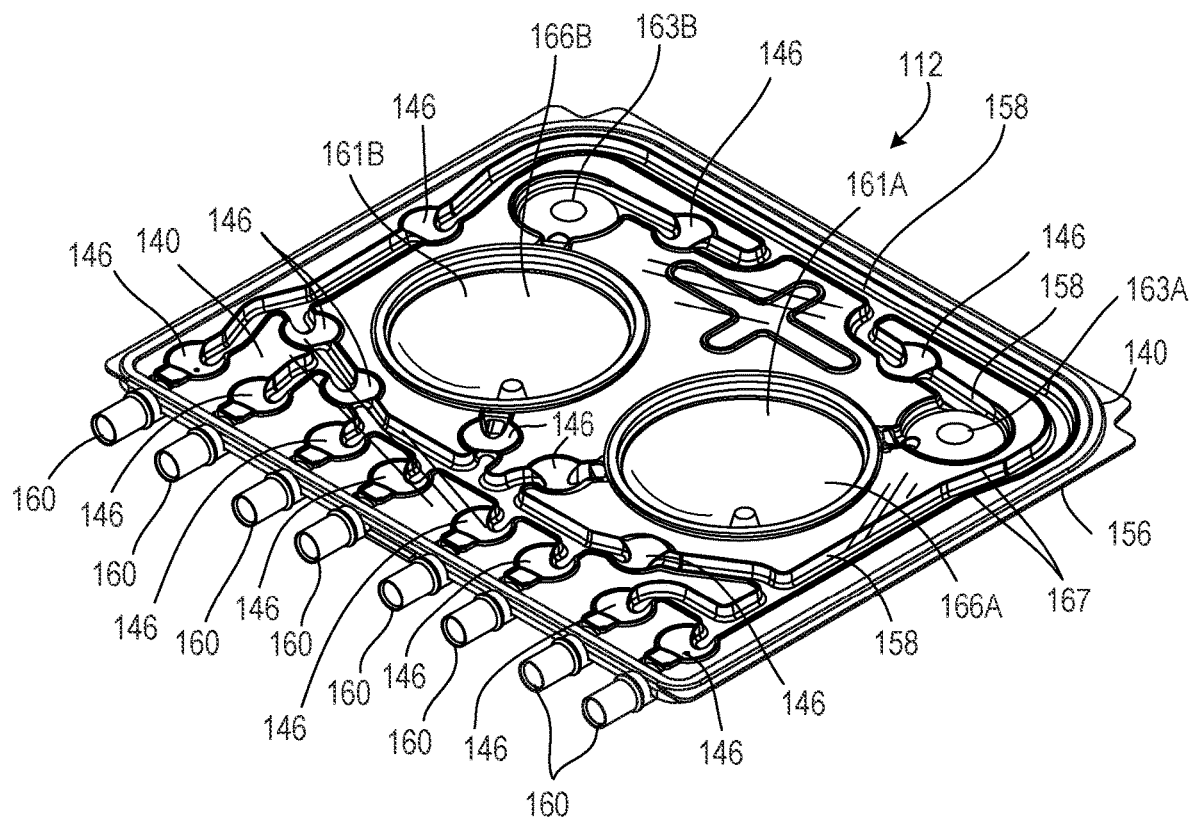
FIGS. 6 and 7 are perspective views of the PD cassette of FIG. 2 from a front side and a back side, respectively, in accordance with some embodiments.
Figure 7:
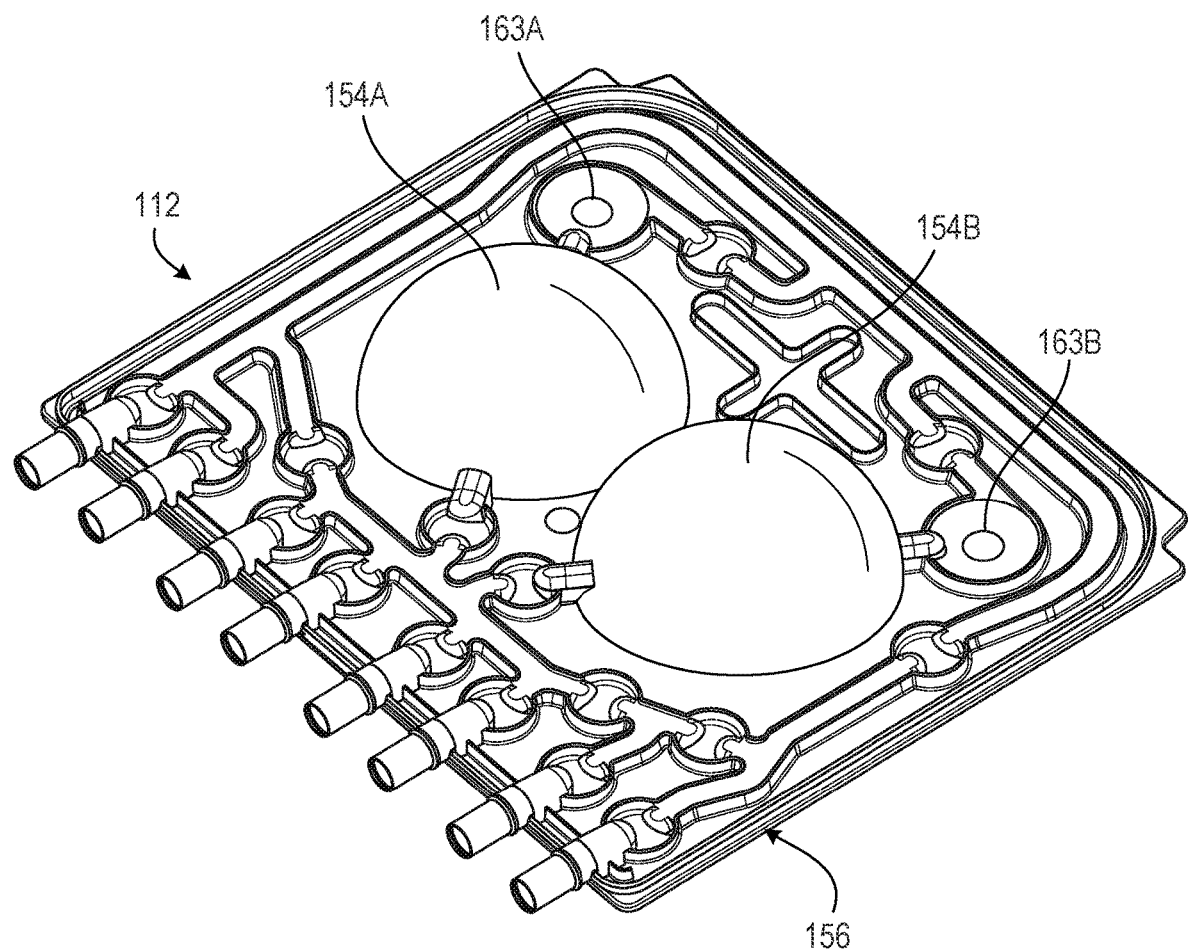

FIG. 4 is an exploded, perspective view of the PD cassette 112 of FIG. 2, in accordance with some embodiments. FIG. 5 is a cross-sectional view of the fully assembled PD cassette 112 of FIG. 2, in accordance with some embodiments. FIGS. 6 and 7 are perspective views of the PD cassette 112 of FIG. 2 from a front side and a back side, respectively, in accordance with some embodiments.

As depicted in FIGS. 4-7, the PD cassette 112 includes a flexible membrane 140 that is attached to a periphery of a tray-like rigid base 156. Rigid dome-shaped fastening members 161A, 161B are positioned within recessed regions 162A, 162B of the base 156. The dome-shaped fastening members 161A, 161B are sized and shaped to receive the piston heads 134A, 134B of the PD machine 102. In some embodiments, the dome-shaped fastening members 161A, 161B have a diameter, measured from the outer edges of annular flanges 164A, 164B, of about 1.5 inches to about 2.5 inches (e.g., about 2.0 inches) and take up about two-thirds to about three-fourths of the area of the recessed regions 162A, 162B. The annular flanges 164A, 164B of the rigid dome-shaped fastening members 161A, 161B are attached in a liquid-tight manner to portions of the inner surface of the membrane 140 surrounding substantially circular apertures 166A, 166B formed in the membrane 140. The annular flanges 164A, 164B of the rigid dome-shaped fastening members 161A, 161B can, for example, be thermally bonded or adhesively bonded to the membrane 140. The apertures 166A, 166B of the membrane 140 expose the rigid dome-shaped fastening members 161A, 161B such that the piston heads 134A, 134B are able to directly contact and mechanically connect to the dome-shaped fastening members 161A, 161B during use.

The annular flanges 164A, 164B of the dome-shaped fastening members 161A, 161B form annular projections 168A, 168B that extend radially inward and annular projections 176A, 176B that extend radially outward from the side walls of the dome-shaped fastening members 161A, 161B. When the piston heads 134A, 134B are mechanically connected to the dome-shaped fastening members 161A, 161B, the radially inward projections 168A, 168B engage the rear angled surfaces of the sliding latches 145A, 147A of the piston heads 134A, 134B to firmly secure the dome-shaped fastening members 161A, 161B to the piston heads 134A, 1334B. Because the membrane 140 is attached to the dome-shaped fastening members 161A, 161B, movement of the dome-shaped fastening members 161A, 161B into and out of the base 156 (e.g., due to reciprocating motion of the pistons 133A, 133B) causes the flexible membrane 140 to similarly be moved into and out of the recessed regions 162A, 162B of the base 156. This movement allows fluid to be forced out of and drawn into the fluid pump chambers 138A, 138B, which are formed between the recessed regions 162A, 162B of the base 156 and the portions of the dome-shaped fastening members 161A, 161B and membrane 140 that overlie those recessed regions 162A, 162B.

Raised ridges 167 extend from the substantially planar surface of the base 156 towards and into contact with the inner surface of the flexible membrane 140 when the cassette 112 is compressed between the door 108 and the cassette interface 110 of the PD machine 102 to form a series of fluid passageways 158 and to form the multiple, depressible dome regions 146, which are widened portions (e.g., substantially circular widened portions) of the fluid pathways 158, as shown in FIG. 6. The fluid passageways 158 fluidly connect the fluid line connectors 160 of the cassette 112, which act as inlet/outlet ports of the cassette 112, to the fluid pump chambers 138A, 138B. As noted above, the various inflatable members 142 of the PD machine 102 act on the cassette 112 during use. The dialysate flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, the flow of the dialysate through the cassette 112 can be controlled through the selective depression of the depressible dome regions 146 by selectively inflating the inflatable members 142 of the PD machine 102.

The fluid line connectors 160 are positioned along the bottom edge of the cassette 112. As noted above, the fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysate bag lines 126, the heater bag line 128, the patient line 130, and the drain line 132. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette 112, as depicted in FIGS. 1 & 2, the connectors 160 allow dialysate to flow into and out of the cassette 112 during use. As the pistons 133A, 133B are reciprocated, the inflatable members 142 can be selectively inflated to allow fluid to flow from any of the lines 126, 128, 130, and 132 to any of ports 185A, 185B, 187A, and 187B of the pump chambers 138A, 138B or to allow fluid to flow from any of ports 185A, 185B, 187A, and 187B of the pump chambers 138A, 138B to any of the lines 126, 128, 130, and 132.

The rigidity of the base 156 helps to hold the cassette 112 in place within the cassette compartment 114 of the PD machine 102 and to prevent the base 156 from flexing and deforming in response to forces applied to the projections 154A, 154B by the dome-shaped fastening members 161A, 161B and in response to forces applied to the planar surface of the base 156 by the inflatable members 142. The dome-shaped fastening members 161A, 161B are also sufficiently rigid that they do not deform as a result of usual pressures that occur in the pump chambers 138A, 138B during the fluid pumping process. Thus, the deformation or bulging of the annular portions 149A, 149B of the membrane 140 can be assumed to be the only factor other than the movement of the pistons 133A, 133B that affects the volume of the pump chambers 138A, 138B during the pumping process.

The base 156 and the dome-shaped fastening members 161A, 161B of the cassette 112 can be formed of any of various relatively rigid materials. In some embodiments, these components of the cassette 112 are formed of one or more polymers, such as polypropylene, polyvinyl chloride, polycarbonate, polysulfone, and other medical grade plastic materials. In some embodiments, these components can be formed of one or more metals or alloys, such as stainless steel. These components can alternatively be formed of various different combinations of the above-noted polymers and/or metals/alloys. These components of the cassette 112 can be formed using any of various different techniques, including machining, molding, and casting techniques.

As noted above, the membrane 140 is attached to the periphery of the base 156 and to the annular flanges 164A, 164B of the dome-shaped fastening members 161A, 161B. The portions of the membrane 140 overlying the remaining portions of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156 and to the dome-shaped fastening members 161A, 161B. The thickness and material(s) of the membrane 140 are selected so that the membrane 140 has sufficient flexibility to flex toward the base 156 in response to the force applied to the membrane 140 by the inflatable members 142. In some embodiments, the membrane 140 is about 0.100 micron to about 0.150 micron in thickness. However, various other thicknesses may be sufficient depending on the type of material used to form the membrane 140. Any of various different materials that permit the membrane 140 to deflect in response to movement of the inflatable members 142 without tearing can be used to form the membrane 140. In some embodiments, the membrane 140 includes a three-layer laminate. In some embodiments, inner and outer layers of the laminate are formed of a compound that is made up of 60 percent Septon® 8004 thermoplastic rubber (i.e., hydrogenated styenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octane copolymer), and 35 percent Septon® 8004 thermoplastic rubber (i.e., hydrogenated styrenic block copolymer). The membrane 140 can alternatively include more or fewer layers and/or can be formed of different materials.

Figure 8:
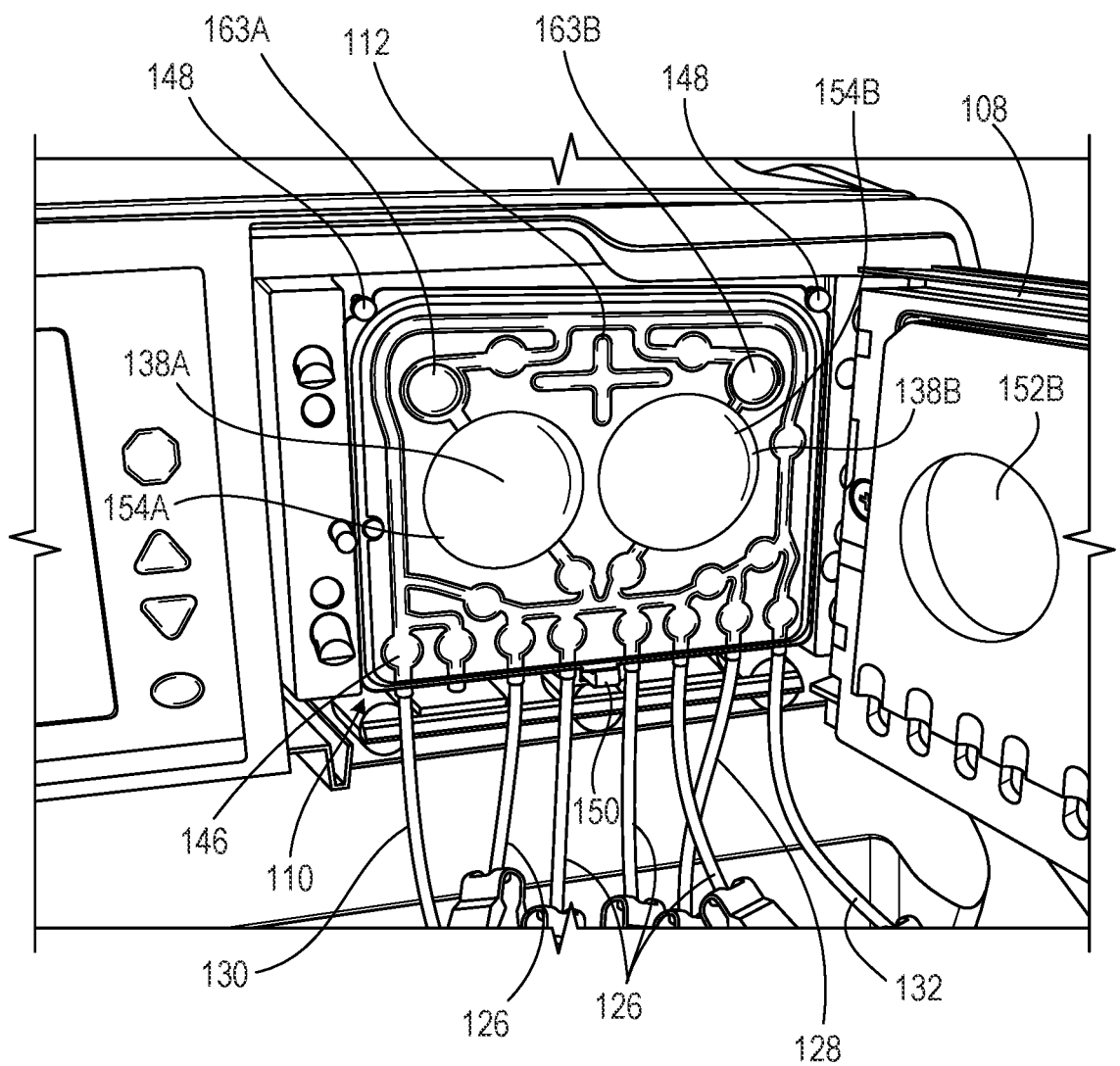
FIG. 8 illustrates the PD cassette seated against the cassette interface, in accordance with some embodiments.

FIG. 8 illustrates the PD cassette 112 seated against the cassette interface 110, in accordance with some embodiments. As depicted in FIG. 8, before starting a PD treatment, the door 108 of the PD machine 102 is opened to expose the cassette interface 110, and the cassette 112 is positioned with the dome-shaped fastening members 161A, 161B aligned with the pistons 133A, 133B of the PD machine 102, the pressure sensing chambers 163A, 163B aligned with the pressure sensors 151A, 151B of the PD machine 102, the depressible dome regions 146 aligned with the inflatable members 142 of the PD machine 102, and the membrane 140 adjacent to the cassette interface 110. In order to ensure that the cassette 112 is properly positioned on the cassette interface 110, the cassette 112 is positioned between the locating pins 148 and the spring loaded latch 150 extending from the cassette interface 110. The asymmetrically positioned connectors 160 of the cassette 112 act as a keying feature that reduces the likelihood that the cassette 112 will be installed with the membrane 140 and dome-shaped fastening members 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward towards the door 108. The pistons 133A, 133B are typically retracted into the piston access ports 136A, 136B during installation of the cassette 112 to avoid interference between pistons 133A, 133B and the dome-shaped fastening members 161A, 161B and, therefore, increase the ease with which the cassette 112 can be positioned within the cassette compartment 114.

After positioning the cassette 112 as desired on the cassette interface 110, the door 108 is closed and the inflatable pad within the door 108 is inflated to compress the cassette 112 between the inflatable pad and the cassette interface 110. The compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146. The patient line 130 is then connected to a patient's abdomen via a catheter, and the drain line 132 is connected to a drain or drain receptacle. In addition, the heater bag line 128 is connected to the heater bag 124, and the dialysate bag lines 126 are connected to the dialysate bags 122. At this point, the pistons 133A, 133B can be coupled to the dome-shaped fastening members 161A, 161B of the cassette 112 to permit priming of the cassette 112 and one or more of the lines 126, 128, 130, and 132. Once these components have been primed, the PD treatment can be initiated.

Smart Connectors

Figure 9:
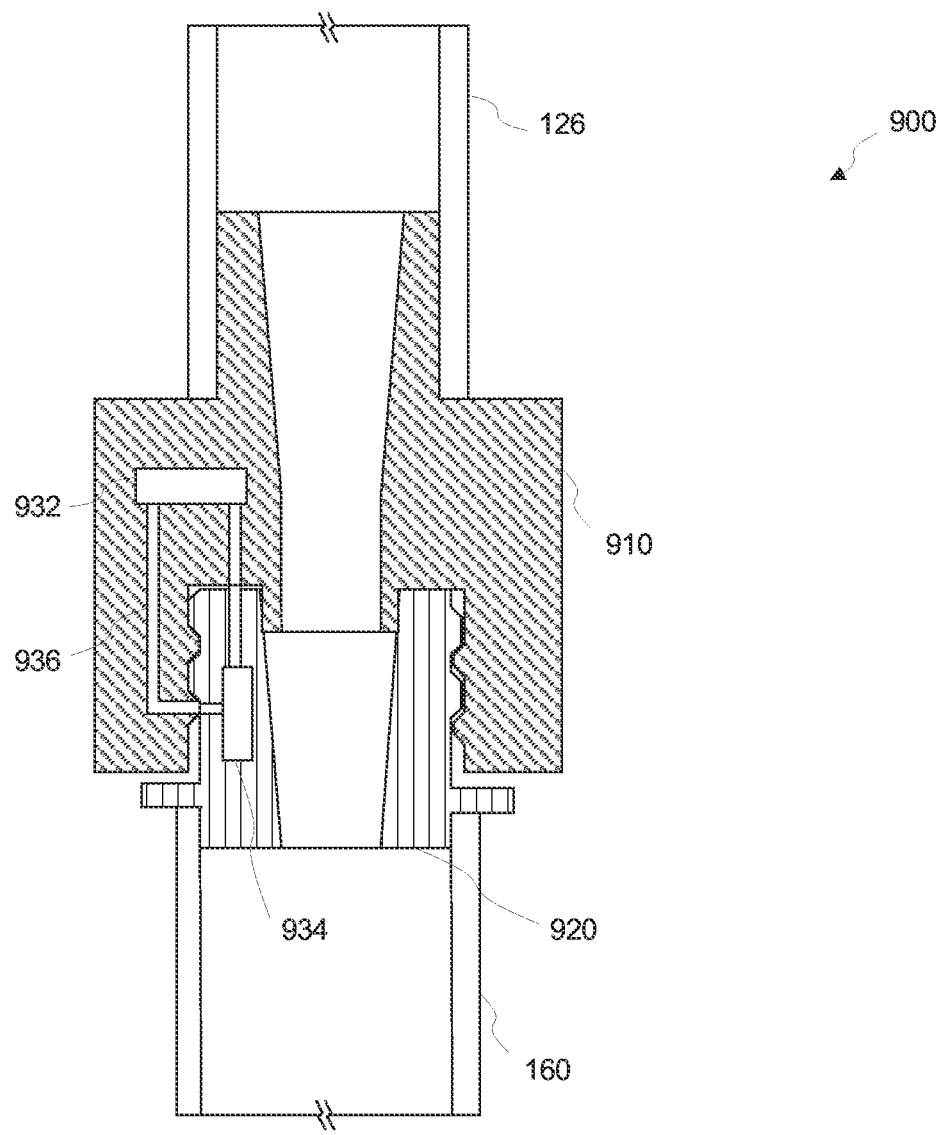
FIG. 9 illustrates a smart connector, in accordance with some embodiments.

FIG. 9 illustrates a smart connector 900, in accordance with some embodiments. The smart connector 900 includes a first portion 910 that mates with a second portion 920. The first portion 910 and the second portion 920 include orifices that promote fluid flow across the smart connector 900. In an embodiment, the first portion 910 is a male connector that is connected on a first end to a distensible tube that is part of or otherwise connected to a dialysate bag line 126. The second portion 920 is a female connector that is connected on a first end to a distensible tube to form a fluid connector 160 that is part of the disposable cassette 112. The second end of the male connector includes a threaded port, and the second end of the female connector is configured to screw into the threaded port. A tapered surface of the orifice in the female connector mates with a protruding structure (e.g., a hollow cylinder) formed inside the threaded port of the male connector such that, when the male connector is mated with (e.g., screwed into) the female connector, the protruding structure is forced into the tapered orifice to form a seal. In some embodiments, the first portion 910 and the second portion 920 conform with a Leur-Lok™ standard (e.g., ISO 8637, ISO 594, ISO 80369, etc.) that defines threaded or unthreaded connectors that include a tapered fitting. It will be appreciated that any type of mating connector can be utilized as a smart connector 900 and that the present disclosure is not limited to existing medical device fittings such as common Leur-Lok™ fittings. Any fluid connector that includes two mated parts is within the scope of the present disclosure.

Unlike conventional connectors, the smart connector 900 includes a radio frequency identifier (RFID) device. The RFID device is split between the first portion 910 and the second portion 920 such that the RFID device is only active (e.g., operational) when the first portion 910 is mated to the second portion 920. In some embodiments, the RFID device comprises a first component 932 and a second component 934 that are in electrical communication via one or more interconnects 936. It will be appreciated that the smart connector 900 is usually formed by injecting a polymer (e.g., cyclic olefin polymer (COP)) into a mold. In some embodiments, the components of the RFID device can be incorporated into the connectors 910/920 via an overmolding manufacturing process. In other words, the components of the RFID device can be placed inside a mold prior to the polymer being injected into the mold such that the RFID device is encapsulated within the hardened polymer that forms the parts of the smart connector 900.

In an embodiment, the first component 932 can include a chip (e.g., integrated circuit, printed circuit, etc.) and the second component 934 can include an antenna. The RFID device is not operational without forming a circuit that includes both the chip and the antenna. In an embodiment, the RFID device is referred to as a passive device, which means that the RFID device receives power from a radio frequency signal provided by a reader device (i.e., the RFID chip operates using power from the electrical signal received via the antenna). In other embodiments, the RFID device can be an active device, which means that a separate power source is included in one of the parts of the connector 900 and used to power the chip. Importantly, the chip is unable to receive or transmit RF signals without being connected to the antenna, and the antenna cannot produce valid RF signals containing formatted information without the chip.

The interconnects 936 are formed from a conducting material such as copper or other metallic wires or sheet metal. Although not shown explicitly, the internal surface of the threaded port of the male connector and the external surface of the threaded portion of the female connector can include terminals (e.g., metal contacts/pads) formed thereon. In some embodiments, the terminals can include a spring or cantilevered metal strip that allows for a certain amount of clearance between the first connector 910 and the second connector 920 while still maintaining electrical contact when the first connector 910 is mated to the second connector 920. In some embodiments, the terminals comprise an annular metallic ring that is molded into the parts 910/920 proximate the threads, prior to the threads being formed. Subsequent to the molding process, the threads are cut into the polymer and metallic rings simultaneously to form the contacts such that, when properly seated, a ring in the male connector overlaps with a corresponding ring in the female connector to form the electrical connection. It will be appreciated that any technically feasible manner for forming contacts to make an electrical connection when the first portion 910 is mated to the second portion 920 is within the scope of the present disclosure.

Figure 10:
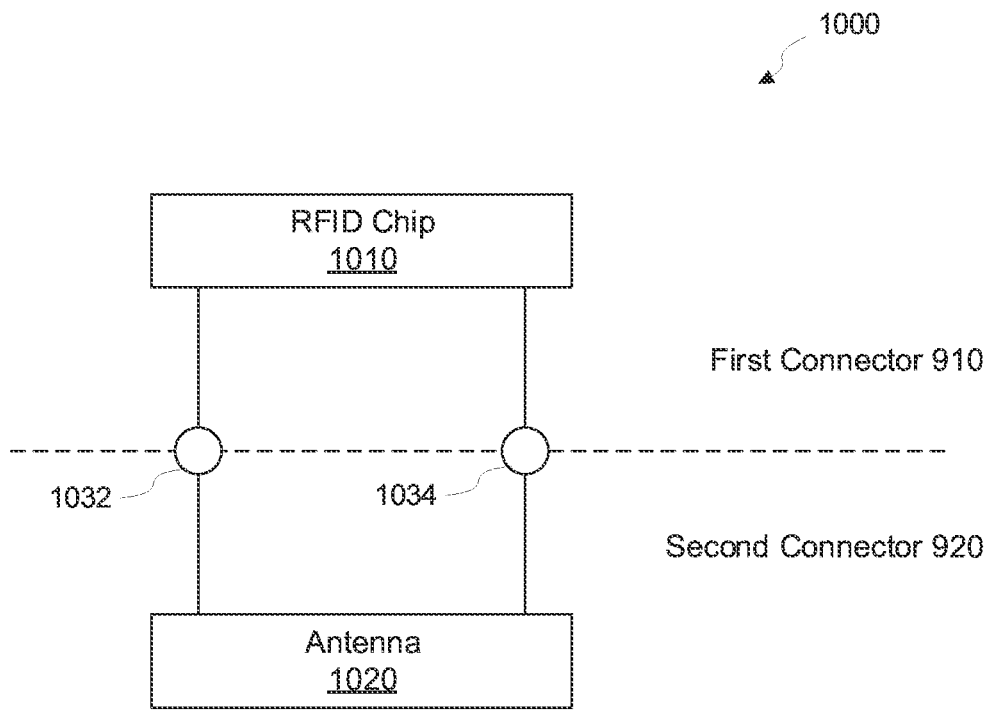
FIG. 10 illustrates a schematic of a split RFID device, in accordance with some embodiments.

FIG. 10 illustrates a schematic of a split RFID device 1000, in accordance with some embodiments. The split RFID device 1000 includes an RFID chip 1010 in a first portion of the connector, such as the first portion 910 of the smart connector 900, and an antenna 1020 in a second portion of the connector, such as the second portion 920 of the smart connector 900. Electrical signals are passed between the RFID chip 1010 and the antenna 1020 via one or more terminals 1032/1034. As shown in FIG. 10, two terminals are provided between the RFID chip 1010 and the antenna 1020. However, in other embodiments, three or more terminals may be provided between the RFID chip 1010 and the antenna 1020. In such embodiments, the antenna can include more than the conductors for the physical antenna, but can also include additional components such as a chip that includes one or more filters (e.g., bandpass filters), a memory that includes an identifier of the port on the disposable cassette, or the like. Any number of terminals can be provided in the physical interface between the connectors, assuming that the terminals are sufficiently isolated electrically and can be formed into the connectors.

Although not shown explicitly, the RFID chip can include or otherwise be connected to a memory internal to the first portion 910. The memory can include information that specifies the type of dialysate included in the bag connected to the dialysate bag line 126 that is attached to the second end of the first portion 910 of the connector 900. For example, the information can include a number of bits (e.g., 4 bits) that can specify an index (e.g., 0-15) for each of a number of configurations. Table 1, shown below, provides an example of the types of dialysate bags that can be identified with 3-bits of information:

TABLE 1

| Description | Index |
|---|---|
| 1.5% Dextrose, 5 L | 0 |
| 1.5% Dextrose, 6 L | 1 |
| 2.5% Dextrose, 5 L | 2 |
| 2.5% Dextrose, 6 L | 3 |
| Dextrose, Low Mg/Ca, 2 L | 4 |
| Dextrose, Low Mg/Ca, 3 L | 5 |
| Dextrose, Low Mg/Ca, 5 L | 6 |
| 1.5% Dextrose, Low Mg/Ca, 6 L | 7 |
| 2.5% Dextrose, Low Mg/Ca, 2 L/3 L | 8 |
| 2.5% Dextrose, Low Mg/Ca, 3 L | 9 |
| 2.5% Dextrose, Low Mg/Ca, 5 L | 10 |
| 2.5% Dextrose, Low Mg/Ca, 6 L | 11 |
| 4.25% Dextrose, Low Mg/Ca, 2 L/3 L | 12 |
| 4.25% Dextrose, Low Mg/Ca, 3 L | 13 |
| 4.25% Dextrose, Low Mg/Ca, 5 L | 14 |
| 4.25% Dextrose, Low Mg/Ca, 5 L | 15 |

Table 1 shows that five different types of dialysate solution, in up to 5 different volumes, can be coded into a 4-bit code represented by the indices 0-15. Alternative, the information can be split into two 3-bit codes, where a first code represents the type of dialysate solution in the bag and a second code represents the volume of the dialysate bag. It will also be understood that the codes used to transmit the information within an RFID signal (referred to as a tag) are not limited to 4 or 6 bits, and that any number of bits capable of being stored in the RFID chip and transmitted within the RFID signal can be mapped to different configurations of dialysate solution. In other cases, the RFID signal includes enough bandwidth to transmit a clear text descriptor for the formulation and/or volume of the dialysate bag, where the descriptor includes up to a specified number of characters. While using a clear text descriptor can require a much larger number of bits (e.g., one byte per character), such embodiments are possible if the RFID signal has sufficient bandwidth to transmit that amount of information and the memory included in the RFID chip is sufficient to store the descriptor.

Figure 11:
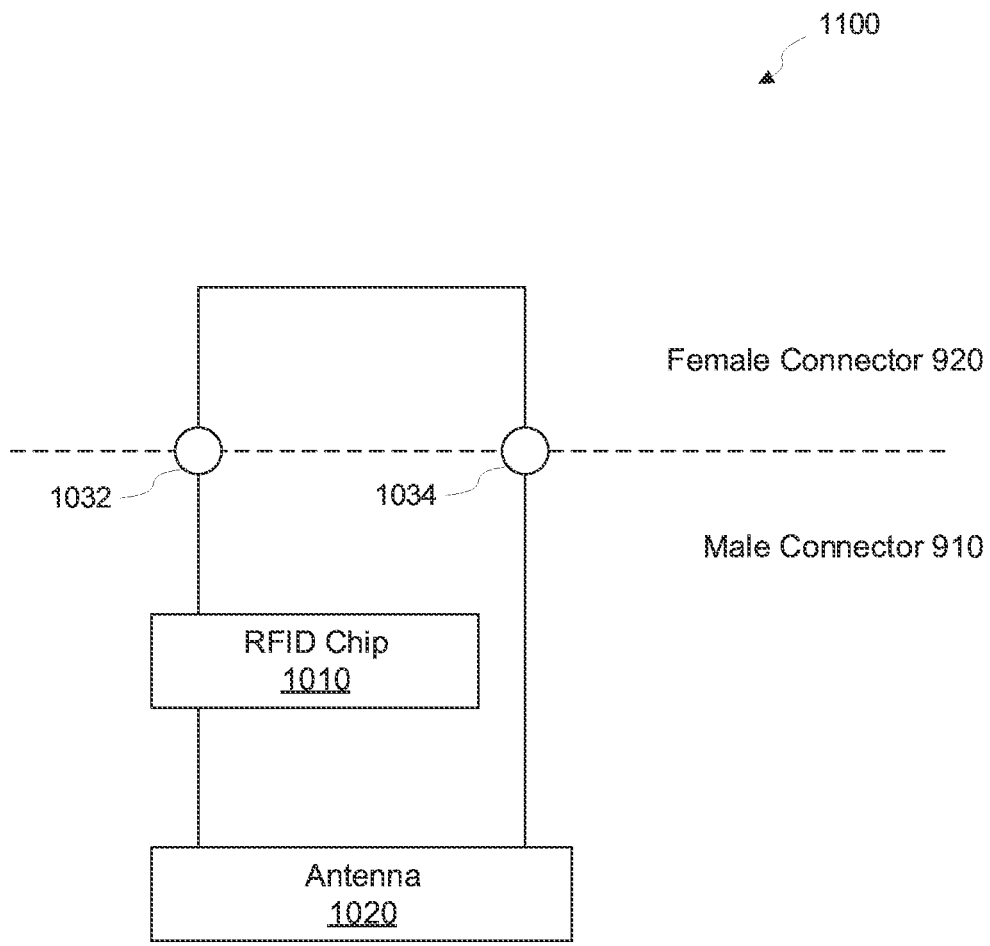
FIG. 11 illustrates a schematic of a split RFID device, in accordance with another embodiment.

FIG. 11 illustrates a schematic of a split RFID device 1100, in accordance with another embodiment. It will be appreciated that the important aspect of the split RFID device 1000 is that the passive RFID device is only active once the first portion 910 and the second portion 920 are mated. While separating the RFID chip 1010 and the antenna 1020 is one method for achieving that goal, other configurations of the RFID device that split the components between the first portion 910 and the second portion 920 are within the scope of the present disclosure.

In an embodiment, the RFID device 1100 includes both the RFID chip 1010 and the antenna 1020 in the first portion 910 of the connector 900. While the major components of the RFID device 1100 are both included in the same portion of the connector 900, the interconnect for routing the RFID signal to the antenna is routed through the terminals 1032/1034 and the second portion 920 of the connector 900. For example, a ground plane of the antenna 1020 can be connected to a ground plane of the RFID chip 1010 without routing the interconnect between the ground planes out of the first portion 910 of the connector 900. Only the interconnect for the RFID signal is routed from the RFID chip 1010 to a first terminal 1032 in the first portion 910, the RFID signal is routed from the first terminal 1032 to the second terminal 1034 in the second portion 920, and the RFID signal is routed from the second terminal 1034 to the antenna 1020 in the first portion 910, which is used to transmit the RFID signal to a reader via the wireless interface.

It will be appreciated that because the RFID chip 1010 is located in the first portion 910 of the connector 900 (i.e., attached to the dialysate bag), the memory storing the information that can be used to encode the identification of the dialysate bag formulation and/or volume can be stored directly in a memory of the RFID chip 1010. Further, in other embodiments, the memory storing the information can be separate from the RFID chip 1010 (but still included in the first portion 910 of the connector 900).

Figure 12:
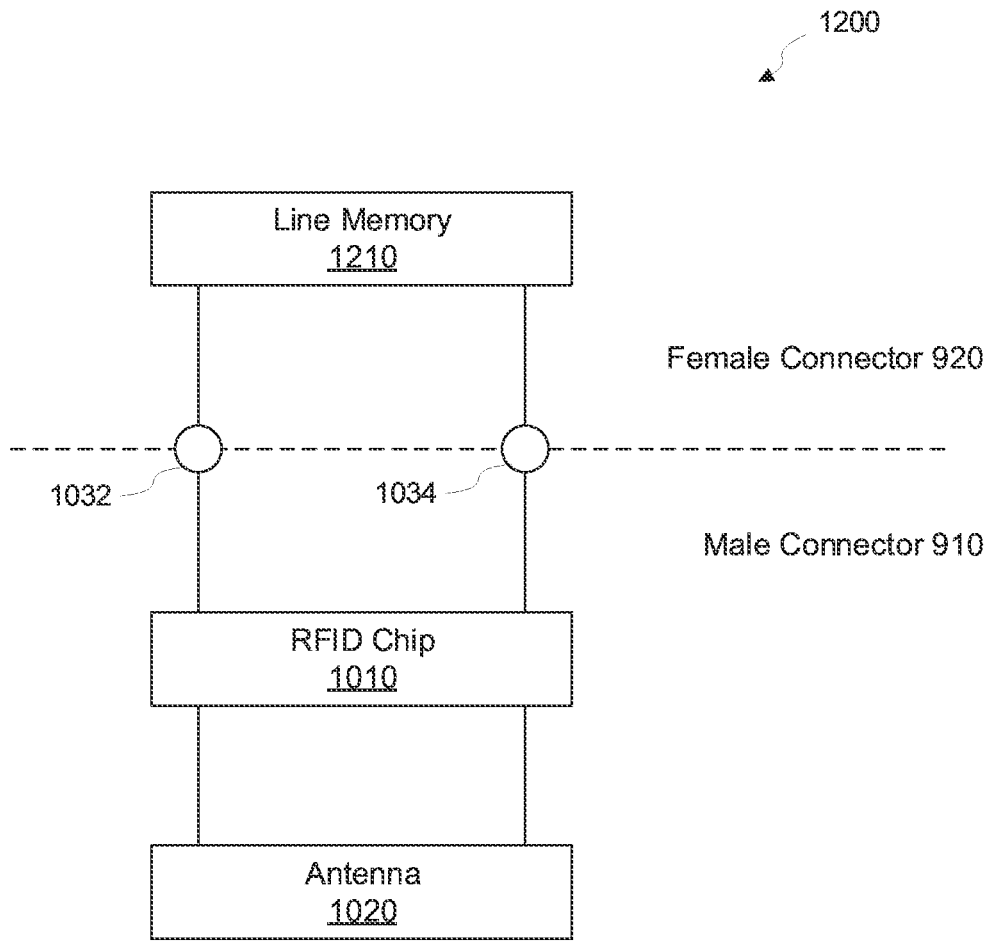
FIG. 12 illustrates a schematic of a split RFID device, in accordance with another embodiment.

FIG. 12 illustrates a schematic of a split RFID device 1200, in accordance with another embodiment. With an embodiment like the RFID device 1100, there are no components of the RFID device 1100, other than the interconnect for the path of the RFID signal to the antenna 1020, in the second portion 920 of the connector 900 that is attached to the disposable cassette 112. Consequently, there is no way for the PD machine 102 to determine, directly from the RFID signal, which port of the cassette 112 the dialysate bag is connected to when the patient or caregiver connects the dialysate bag line 126 to the cassette 112 by mating the first portion 910 with the second portion 920 of the connector 900. It will be appreciated that, in some configurations of the cassette 112 and PD machine 102, connecting the dialysate bag line 126 to the fluid connector 160 of the cassette 112 can allow fluid to flow from the dialysate bag into the cassette 112, where a separate sensor can detect fluid flow or fluid pressure in a chamber of the cassette 112. The PD machine 102 can then infer which port of the cassette 112 the dialysate bag was just connected to, based on the transitions of the sensor signals. However, such sensing only provides an indirect measurement for detecting which port that a dialysate bag was connected to when an RFID signal is received after a first portion 910 is mated to a second portion 920 of the connector 900. Furthermore, depending on the configuration of the cassette 112 and the sensors included in the PD machine 102, the PD machine 102 may not be capable of differentiating between multiple different dialysate bag lines based on an indirect measurement of a sensor signal having a different primary purpose. In such cases, it may be beneficial to provide information on both the formulation and/or volume of the dialysate bag as well as an indication of the particular port of the cassette 112 that the dialysate bag was connected to within the RFID signal (i.e., the tag) itself.

In a split RFID device 1200, first information for identifying the formulation and/or volume of the dialysate bag can be stored in the first portion 910 of the connector 900 and second information for identifying the particular port of the cassette 112 can be stored in the second portion 920 of the connector 900. The RFID chip 1010 can then read the first information from a memory included in the first portion 910 and read the second information from a memory included in the second portion 920 to generate combined information that is encoded into the RFID signal.

As shown in FIG. 12, the RFID chip 1010 and the antenna 1020 can be included in the first portion 910 and a memory (e.g., a line memory 1210) is included in the second portion 920. The first information can be stored directly in the RFID chip 1010 and the second information is stored in the line memory 1210. It will be appreciated that, based on the connection of the RFID chip 1010 and the antenna 1020, the RFID chip 1010 and antenna 1020 could be operational (i.e., capable of generating an RFID signal over the wireless interface) without the line memory 1210 and without the first portion 910 being mated with the second portion 920. In this embodiment, the RFID chip 1010 should be designed to transmit an RFID signal via the antenna 1020 only when the RFID chip can access the line memory 1210, which ensures that the RFID device 1200 is only operational when the first portion 910 is mated to the second portion 920, via the use of software or fixed function hardware (i.e., logic circuits) implemented by the RFID chip 1010. In other words, while the circuit theoretically allows the RFID chip 1010 and the antenna 1020 to function without being connected to the second portion 920 of the connector 900, the logic implemented by the RFID chip 1010 prevents the RFID chip 1010 from sending a response to the reader unless the line memory 1210 is detected as being connected to the RFID chip 1010.

In other embodiments, the circuit of FIG. 12 can be modified to route the interconnect between the RFID chip 1010 and the antenna 1020 through the second portion 920, similar to the configuration shown in FIG. 11. This would require two additional terminals in addition to the two terminals included to route the second information from the line memory 1210 to the RFID chip 1010. However, such a modification would simplify the design of the logic of the RFID chip 1010 as functionality of the RFID tag 1200 would ensure that the first portion 910 was properly mated with the second portion 920, rather than relying on software or logic designed into a fixed function circuit to enable or disable the RFID device 1200.

It will be appreciated that there are many different options for ways to split the components of the RFID tag across a connection interface of the smart connector 900. However, the component that stores the information about the dialysate bag (e.g., formulation/volume) must be included in the side of the connector attached to the dialysate bag because the disposable cassette 112 is a separate component of the combined fluid pathway through the PD machine 102. In other words, the minimum requirement of the smart connector 900 is that the portion of the connector permanently attached to a dialysate bag, whether that portion is a male connector or a female connector, includes the stored information related to the dialysis bag that is transmitted over the wireless signal to a reader. That information can be stored in a dedicated memory separate from the RFID chip or within the RFID chip itself, and the RFID chip can be included separate from or integrated with the antenna, but at least one component required to make the RFID tag operation must be located on each side of the smart connector interface. For example, in some embodiments, the RFID chip and antenna can be included in the portion of the connector attached to the cassette 112, but in such embodiments the RFID chip must be able to access a memory in the portion of the connector attached to the dialysate bag that stores the information about the dialysate bag.

Figure 13:
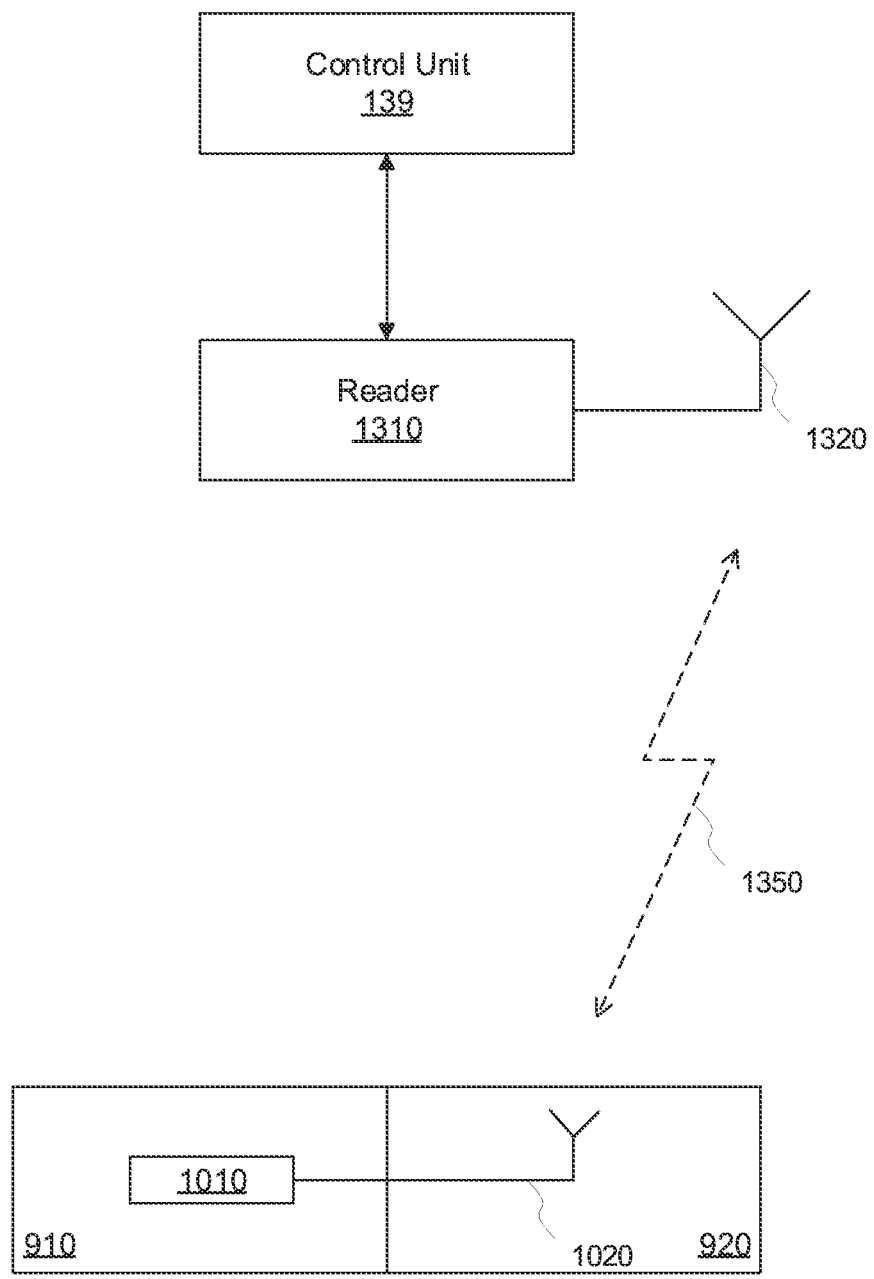
FIG. 13 illustrates a system for reading the RFID tag incorporated into the smart connector, in accordance with an embodiment.

FIG. 13 illustrates a system 1300 for reading the RFID tag incorporated into the smart connector 900, in accordance with an embodiment. The system 1300 includes the smart connector 900 and a near field communication (NFC) device 1310. The NFC device 1310 can be included in the PD machine 102 and is configured to communicate with the RFID chip 1010 in the smart connector 900 via a wireless interface 1350. As used herein, the wireless interface can be implemented by a transceiver (e.g., receiver/transmitter) and antenna 1320 connected to the NFC device 1310. The antenna 1320 is used to send and receive RF signals via the wireless interface 1350 to the antenna 1020 of the smart connector 900.

In an embodiment, the NFC device 1310 can be designed to operate in a frequency band at 13.56 MHz, with a 14 kHz bandwidth. The NFC device 1310 can be referred to as a reader or an NFC reader. The NFC device 1310 transmits a RF signal over the wireless interface 1350. If the first portion 910 is mated to the second portion 920 of the smart connector 900, then the antenna 1020 receives the RF signal, which provides power to the RFID chip 1010. The RFID chip 1010 operates to generate an RFID signal that is transmitted back to the NFC device 1310 via the antenna 1020, where the RFID signal includes information that identifies the dialysate bag attached to the first portion 910 of the smart connector 900 and, optionally, additional information that identifies the specific port on the disposable cassette 112 connected to the second portion 920 of the smart connector 900.

In other embodiments, the NFC device 1310 can be replaced with a reader that operates in a different frequency band, such as using a low frequency signal (e.g., between 30 kHz and 300 kHz), a high frequency signal (e.g., between 3 MHz and 30 MHz), or an ultra-high frequency signal (e.g., between 300 MHz and 3 GHz). Higher frequency signals generally have a lower range compared with lower frequency signals. However, given that the reader is generally incorporated into the PD machine 102 and will be proximate the smart connector 900, readers in the high frequency range (e.g., NFC at 13.56 MHz) or ultra-high frequency (UHF) range may be optimally selected for use in the PD machine 102.

In an embodiment, the NFC device 1310 is connected to the control unit 139 of the PD machine 102. The control unit 139 can be configured to prompt the user (e.g., patient or caregiver) to connect a dialysate bag to the cassette 112 prior to beginning a PD treatment. The control unit 139 sends a signal to the NFC device 1310 to monitor the wireless interface 1350 to detect the connection of a smart connector 900. In an embodiment, the NFC device 1310 is configured to periodically (e.g., every 3 seconds) transmit a RF signal over the wireless interface 1350 to attempt to detect a new connection. A new connection is detected when the NFC device 1310 receives a response from the RFID chip 1010 included in the smart connector 900. It will be appreciated that multiple dialysate bags can be connected to the cassette 112 simultaneously and, therefore, multiple RFID chips from multiple smart connectors 900 attached to the cassette 112 can respond to the RF signal broadcast by the NFC device 1310. In an embodiment, the NFC device 1310 is configured to collect information from each RFID chip that responds to the RF signal and store a history of RFID tags corresponding to dialysate bags currently connected to the cassette 112. For each RFID tag received by the NFC device 1310, the NFC device 1310 compares the received information (e.g., the tag) to stored tags in the history to determine if the tag is associated with a new connection. If the tag is associated with a new connection, then the NFC device 1310 can store the tag in the history and notify the control unit 139 of the detection of a new connection as well as provide the control unit 139 with the information encoded in the tag.

In addition, if the NFC device 1310 fails to receive a response from an RFID chip corresponding to any tag stored in the history for a period of time (e.g., a time corresponding to one or more RF signals transmitted by the NFC device 1310), then the NFC device 1310 can delete that tag from the history to indicate that the corresponding RFID chip has been disconnected from the cassette 112 (i.e., the male connector for the corresponding dialysate bag was disconnected from the female connector of the cassette 112). Consequently, the next time the NFC device 1310 receives that tag in a response to the RF signal, the NFC device 1310 will detect that the tag is a new connection.

Figure 14:
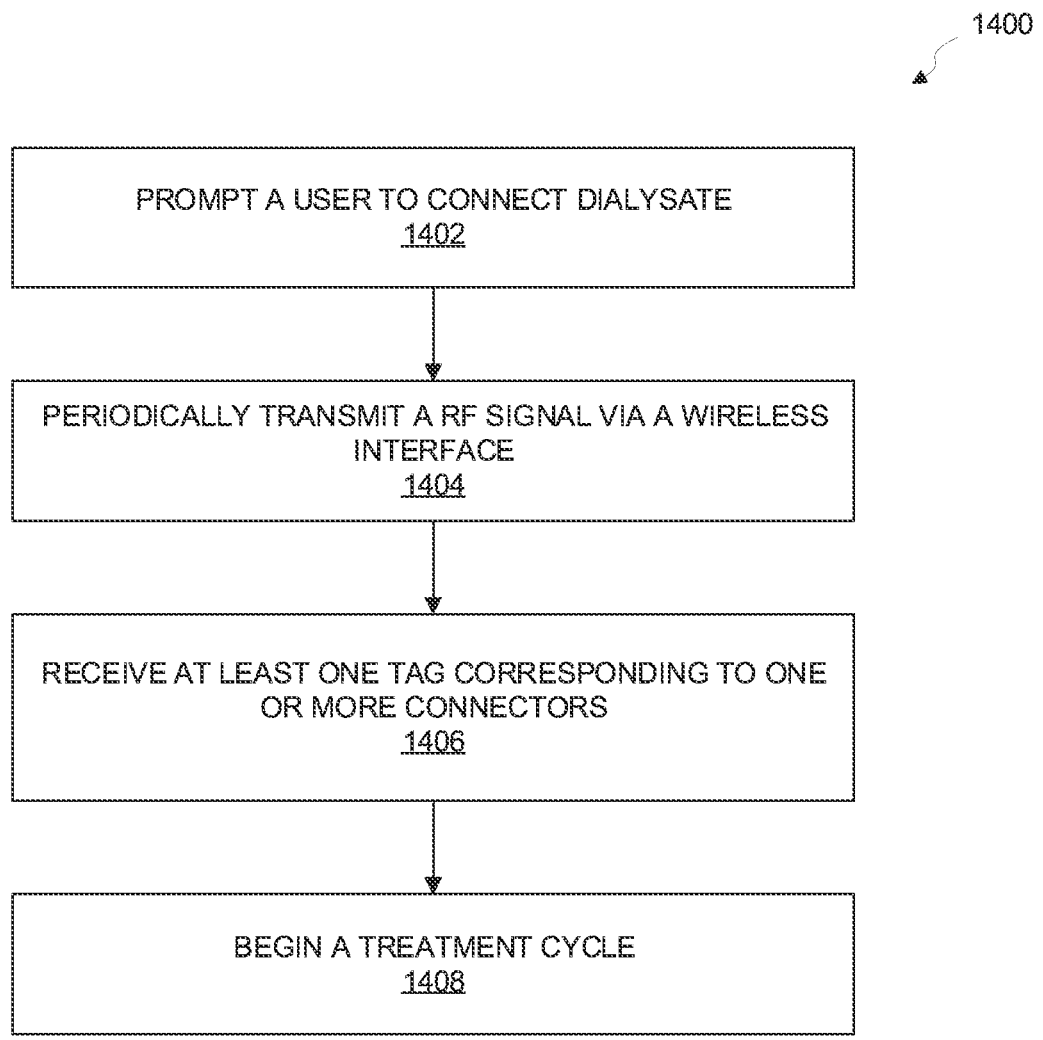
FIG. 14 is a flow diagram of a method for operating a dialysis machine, in accordance with some embodiments.

FIG. 14 is a flow diagram of a method 1400 for operating a dialysis machine, in accordance with some embodiments. It will be appreciated that the method 1400 is described as being performed by the PD machine 102. More specifically, the various steps described below can be implemented by a processor, such as the control unit 139 of the PD machine 102, configured to execute a number of instructions. In various embodiments, the method 1400 can be implemented using hardware, software executed by a general purpose processor configured to control a specialized apparatus such as a PD machine, or a combination of hardware and software.

At step 1402, a user is prompted to connect dialysate (e.g., dialysate bags) to a dialysis machine. In an embodiment, the PD machine 102 displays a message on a touchscreen that asks a user to connect a dialysate bag to the cassette 112. If more than one dialysate bag is connected to the cassette 112, then the prompt can indicate the formulation and/or volume of the dialysate bag to connect as well as which port of a plurality of ports of the cassette 112 on which to connect the dialysate bag. In some embodiments, the prompt can be provided via an audio message instead of or in addition to a visual indication. In other embodiments, step 1402 can be omitted, assuming that the patient or caregiver has been provided instructions for what to connect by their doctor or a pharmacist.

At step 1404, the dialysis machine periodically transmit an RF signal over a wireless interface. The RF signal can be a request to one or more RFID devices within range of the dialysis machine to transmit an RFID signal including a tag to the dialysis machine. In an embodiment, the RF signal can be formatted according to a standard for RFID devices, such as a standard for NFC tags.

At step 1406, the dialysis machine receives, via the wireless interface, at least one tag corresponding to the one or more connectors. In an embodiment, when a user mates a first portion of a smart connector attached to a dialysate bag to a second portion of the smart connector attached to a port of the cassette, the RFID device split across the two portions of the smart connector is enabled (e.g., operational) and is configured to respond to the RF signal transmitted by the dialysis machine by transmitting the RFID signal that includes a tag stored in the RFID device. In an embodiment, the tag can include first information that identifies at least one of the formulation of a dialysate bag as well as a volume of the dialysate solution included in the dialysate bag. The tag can also optionally include second information that indicates the port of the cassette connected to the second portion of the smart connector.

Optionally, steps 1404 and 1406 can be repeated until a set number of connectors have responded to the RF signal, indicating an expected number of connections have been made by the user (e.g., patient or care giver). For example, if two dialysate bags are expected to be connected, the dialysis machine can periodically re-transmit the RF signal over the wireless interface until receiving at least two separate tags from the two connectors attached to the two separate dialysis bags. In some embodiments, connectors for other lines, such as the patient line, a heater bag line, and/or a drain line can also be confirmed to have been connected based on separate tags returned by corresponding RFID devices in those connectors.

At step 1408, the dialysis machine initiates a treatment cycle by, e.g., operating the dialysate machine in accordance with the information received from the smart connectors. For example, the number of treatment cycles can be paused when the amount of dialysate drained from a dialysate bag exceeds an amount calculated by the machine based on the tag information received through a tag. In another example, the dialysis machine can select a source of dialysate based on the detected connections.

Figure 15:
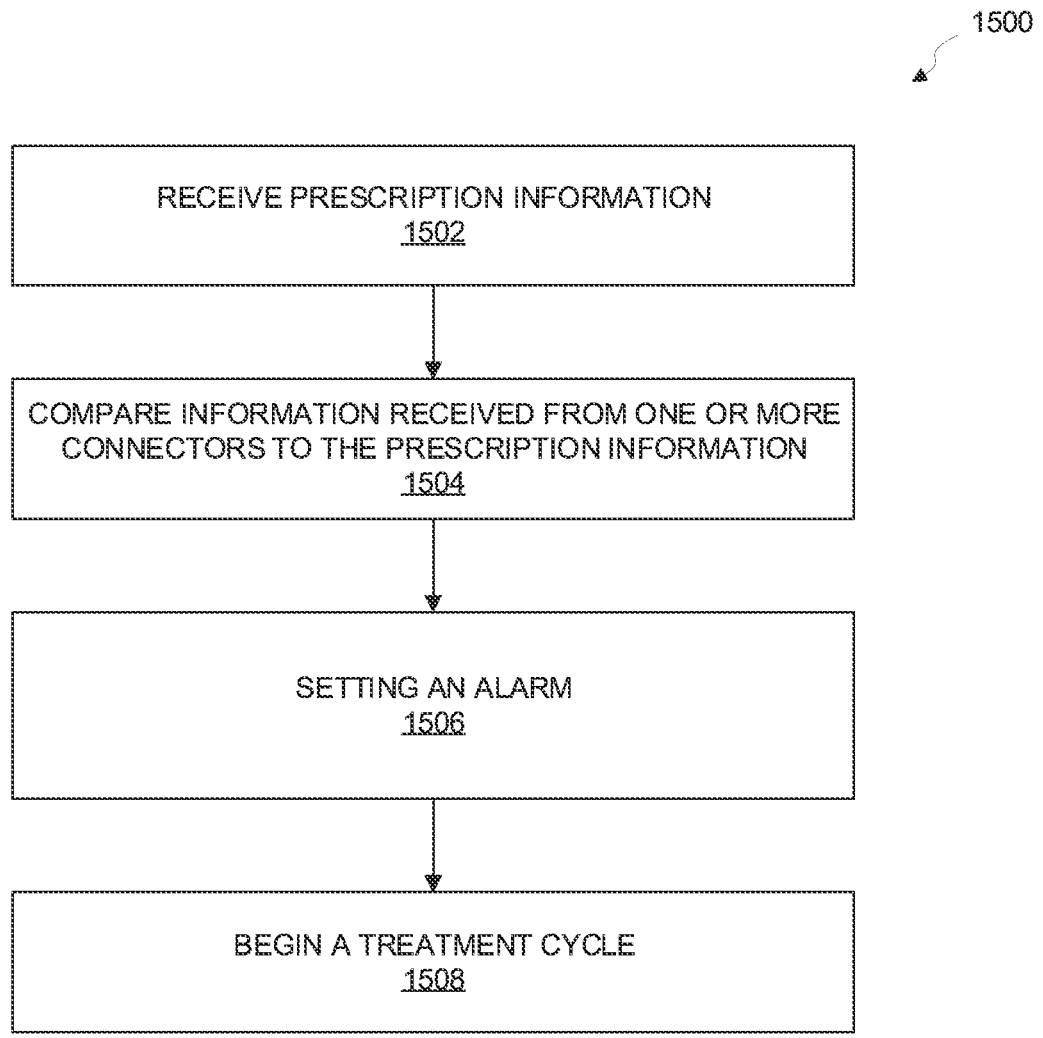
FIG. 15 is a flow diagram of a method for operating a dialysis machine, in accordance with some embodiments.

FIG. 15 is a flow diagram of a method 1500 for operating a dialysis machine, in accordance with some embodiments. It will be appreciated that the method 1500 is described as being performed by the PD machine 102. More specifically, the various steps described below can be implemented by a processor, such as the control unit 139 of the PD machine 102, configured to execute a number of instructions. In various embodiments, the method 1500 can be implemented using hardware, software executed by a general purpose processor configured to control a specialized apparatus such as a PD machine, or a combination of hardware and software.

At step 1502, a dialysis machine receives prescription information. In an embodiment, the prescription information can be stored in a USB device that is plugged into a USB port of the dialysis machine. In another embodiment, the prescription information can be sent to the dialysis machine over a network, such as transmitted to the PD machine 102 over a network such as the Internet via a wireless connection. The prescription information can indicate the type and amount of dialysate provided to the patient for use in a treatment.

At step 1504, information received from one or more connectors is compared against the prescription information. In an embodiment, the information received from the one or more connectors includes tags from each connector that indicates at least one of the formulation and/or volume of the dialysate bags connected to the dialysis machine.

If the information indicates that the dialysate bags connected to the dialysis machine do not match the expected configuration indicated by the prescription information, then, at step 1506, the dialysis machine can set an alarm indicating that the dialysate bags may not be of the correct type and/or have sufficient volume to complete the prescribed treatment. However, if the information matches the prescription information or the user changes the connections to match the prescription information in response to the alarm, then, at step 1508, the dialysis machine can initiate a treatment cycle.

It will be appreciated that the dialysis machine, by having the ability to automatically read the information identifying the dialysate bags connected to the dialysis machine, can perform safety checks against provided prescription information to ensure that the treatment being administered is the intended treatment that was prescribed by the patient's doctor. Such operation can help to prevent unsafe practices that result from user error.

Figure 16:
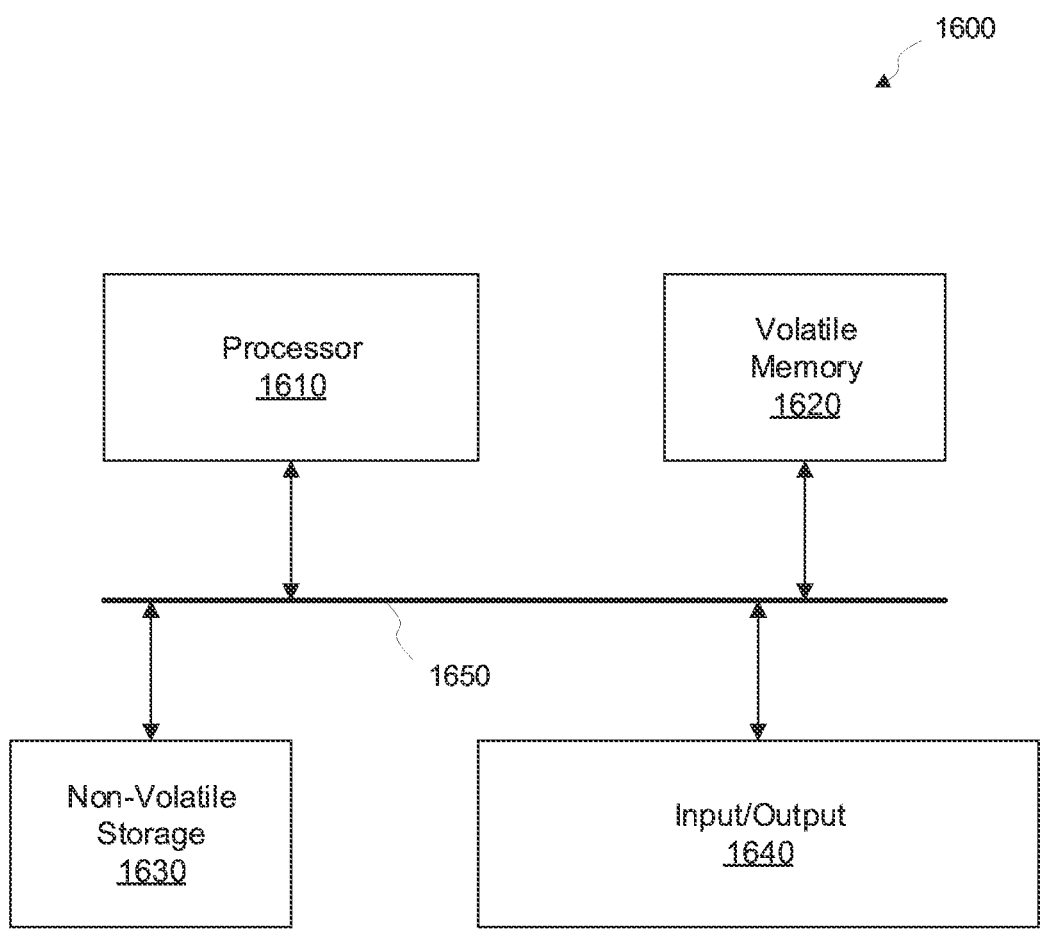
FIG. 16 illustrates an exemplary computer system, in accordance with some embodiments.

FIG. 16 illustrates an exemplary computer system 1600, in accordance with some embodiments. It will be appreciated that, in various embodiments, the control unit 139 can be implemented, at least in part, to include the components of the computer system 1600. The processor 1610 can execute instructions that cause the computer system 1600 to implement the functionality of the control unit 139, as described above.

As depicted in FIG. 16, the system 1600 includes a processor 1610, a volatile memory 1620, a non-volatile storage 1630, and one or more input/output (I/O) devices 1640. Each of the components 1610, 1620, 1630, and 1640 can be interconnected, for example, using a system bus 1650 to enable communications between the components. The processor 1610 is capable of processing instructions for execution within the system 1600. The processor 1610 can be a single-threaded processor, a multi-threaded processor, a vector processor that implements a single-instruction, multiple data (SIMD) architecture, a quantum processor, or the like. The processor 1610 is capable of processing instruction stored in the volatile memory 1620. In some embodiments, the volatile memory 1620 is a dynamic random access memory (DRAM). The instructions can be loaded into the volatile memory 1620 from the non-volatile storage 1630. In some embodiments, the non-volatile storage 1630 can comprise a flash memory such as an EEPROM. In other embodiments, the non-volatile storage 1630 can comprise a hard disk drive (HDD), solid state drive (SSD), or other types of non-volatile media. The processor 1610 is configured to execute the instructions, which cause the PD machine 102 to carry out the various functionality described above.

In some embodiments, the memory 1620 stores information for operation of the PD machine 102. For example, operating parameters can be stored in the memory 1620. The processor 1610 can read the values of the operating parameters from the memory 1620 and then adjust the operation of the PD machine 102 accordingly. For example, a speed of the pistons 133A, 133B can be stored in or written to the memory 1620 and read from the memory 1620. The speed is then used to control signals transmitted to the stepper motor drivers.

The I/O device(s) 1640 provides input and/or output interfaces for the system 1600. In some embodiments, the I/O device(s) 1640 include a network interface controller (NIC) that enables the system 1600 to communicate with other devices over a network, such as a local area network (LAN) or a wide area network (WAN) such as the Internet. In some embodiments, the non-volatile storage 1630 can include both local and remote computer readable media. The remote computer readable media can refer to a network storage device such as a storage area network (SAN) or a cloud-based storage service. The I/O device(s) 1640 can also include, but are not limited to, a serial communication device (e.g., RS-232 port, USB host, etc.), a wireless interface device (e.g., a transceiver conforming to Wi-Fi or cellular communication protocols), a sensor interface controller, a video controller (e.g., a graphics card), or the like.

It will be appreciated that the system 1600 is merely one exemplary computer architecture and that the control unit 139 or other processing devices can include various modifications such as additional components in lieu of or in addition to the components shown in FIG. 16. For example, in some embodiments, the control unit 139 can be implemented as a system-on-chip (SoC) that includes a primary integrated circuit die containing one or more CPU core, one or more GPU cores, a memory management unit, analog domain logic and the like coupled to a volatile memory such as one or more SDRAM integrated circuit dies stacked on top of the primary integrated circuit dies and connected via wire bonds, micro ball arrays, and the like in a single package (e.g., chip). The chip can be included in a chipset that includes additional chips providing the I/O device 1640 functionality when connected to the SoC via a printed circuit board.

Figure 17:
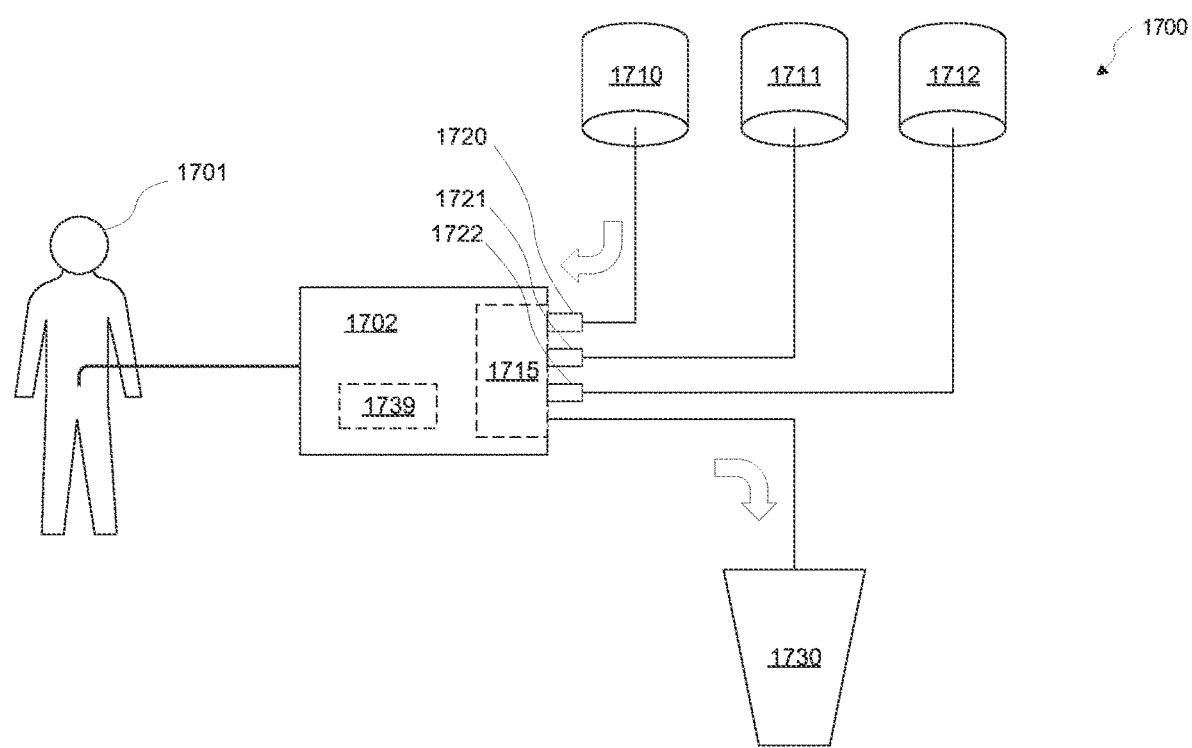
FIG. 17 is a schematic illustration showing a dialysis system with which the smart dialysis bag detection system described herein may be utilized, according to an implementation of the present disclosure.

FIG. 17 is a schematic illustration showing a dialysis system 1700 with which the smart dialysis bag detection system described herein may be utilized, according to an implementation of the present disclosure. The system 1700 includes a dialysis machine 1702, which may be a PD machine like the dialysis machine 102 discussed elsewhere herein for flowing fresh dialysate into a patient and draining used dialysate out of the patient. One or more dialysate sources may be connected to the dialysis machine 1702. In some embodiments, as illustrated, the dialysate source(s) may be dialysate bags 1710, 1711, 1712 that are disposed near the dialysis machine 1702. In an embodiment, the dialysate bags 1710, 1711, 1712 may be hung which may improve air content management as any air content is disposed by gravity to a top portion of the dialysate bag 1710, 1711, 1712. Additionally and/or alternatively, the dialysate bags 1710, 1711, 1712 may be disposed on shelves below or near the dialysis machine 1702. Valves may be attached to a bottom portion of the dialysate bags 1710, 1711, 1712 so fluid is drawn out and air content delivery is minimized.

The dialysate bags 1710, 1711, 1712 may be connected to a cassette 1715, which may be insertable into the dialysis machine 1702. In use, the cassette 1715 may be connected to dialysate bag lines of the dialysate bags 1710, 1711, 1712 with smart connectors 1720, 1721, 1722, which may be used to pass dialysate from dialysate bags 1710, 1711, 1712 to the cassette 1715, and which may each have features like one or more of the smart connectors discussed elsewhere herein, such as smart connector 900. Although three dialysate bags 1710, 1711, 1712 and three smart connectors 1720, 1721, 1722 are illustrated, the system described herein may be utilized in connection with more or fewer bags and/or connectors. In use, the cassette 1715 may be disposable. Alternatively, the cassette 1715 may be reusable. In addition, a patient line and a drain line may be connected or associated with the cassette 1715. The patient line may be connected to the abdomen of a patient 1701 via a catheter and may be used to pass dialysate back and forth between the cassette 1715 and the patient's peritoneal cavity during use. The drain line may be connected to a drain or drain receptacle 1730 and may be used to pass dialysate from the cassette 1715 to the drain or drain receptacle 1730 during use.

As further described in detail elsewhere herein, information read from tag(s) of the smart connectors 1710, 1711, 1712 by a reader can be utilized by a controller 1739 of the dialysis machine 1702, for example, a controller having features like the control unit 139 discussed elsewhere herein. In an embodiment, the smart connectors 1710, 1711, 1712 enable the storing and reading of information that indicates a formulation or a volume of one or more of the dialysis bags 1710, 1711, 1712 connected to the ports of the cassette 1715 such that the dialysis machine 1702 can automatically discover the configuration of the dialysis setup and/or make automatic changes. For example, by automatically detecting the volume and/or concentration of one or more of the dialysate bags 1710, 1711, 1712 connected to each port of the disposable cassette 1715, the dialysis machine 1702 can determine when a dialysis bag has been drained. As another example, different volumes of dialysate from two or more different dialysate bags 1710, 1711, 1712 with different concentrations of minerals or electrolytes can be mixed to create concentrations between the two source concentrations (e.g., equal volume of 1.5% dextrose and 2.5% dextrose solutions can be mixed to create a 2.0% dextrose solution, or a 10% dextrose solution can be mixed with pure saline to produce a concentration between 0-10%).

The system and techniques described herein are discussed for illustrative purposes principally in connection with a particular type of PD cycler, for example a PD cycler having piston-based pumps and a heater tray used to batch heat dialysate in a heater bag. It is noted that the system and techniques described herein may be suitably used in connection with other types and configurations of dialysis machines and/or medical devices involving the transmission of fluid to and from a patient via a patient line and for which patient line checks and occlusion detection would be beneficially performed. For example, the system and techniques described herein may be used in connection with a PD cycler using a different configuration and style of pump, such as a peristaltic pump, and may be used in connection with other types of dialysate heating arrangements, such as in-line heating arrangements. Further, the system described herein may be suitably used in connection with other types of dialysis machines, including, for example, hemodialysis machines.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A dialysis system, comprising:
    a plurality of dialysate bags;
    a plurality of fluid lines coupled to the plurality of dialysate bags;
    a plurality of connectors attached to the plurality of fluid lines;
    a reader configured to wirelessly access information from the plurality of connectors;
    a disposable cassette having a plurality of ports, wherein each respective port of the plurality of ports is fluidly coupled to a respective connector of the plurality of connectors; and
    a controller configured to:
        receive the accessed information from the reader, wherein the accessed information indicates a first formulation of a first dialysate bag of the plurality of dialysate bags and a second formulation of a second dialysate bag of the plurality of dialysate bags, wherein the first dialysate bag is fluidly coupled to a first port of the plurality of ports via a first connector of the plurality of connectors, and wherein the second dialysate bag is fluidly coupled to a second port of the plurality of ports via a second connector of the plurality of connectors; and
        adjust operation of at least one component of the dialysis system based on the accessed information;
    wherein adjusting the operation of the at least one component of the dialysis system comprises:
        determining that the first formulation of the first dialysate bag is different than the second formulation of the second dialysate bag based on the accessed information; and
        mixing a first volume of the first formulation from the first dialysate bag with a second volume of the second formulation from the second dialysate bag to create a volume of mixed dialysate solution;
    wherein the first connector includes a first tag of a plurality of tags, and the second connector includes a second tag of the plurality of tags;
    wherein each tag of the plurality of tags comprises a chip, a memory, and an antenna, and wherein the memory of a respective tag of the plurality of tags includes multiple bits which specify a respective index of a plurality of indexes, wherein the respective index indicates a respective constituent-concentration-volume combination of a plurality of constituent-concentration-volume combinations, and wherein the respective constituent-concentration-volume combination indicates that a respective corresponding dialysate bag of the plurality of dialysate bags contains a respective volume of a respective formulation and that the respective formulation includes a respective constituent at a respective concentration.

2. The dialysis system of claim 1, wherein the reader is a near field communication (NFC) device configured to:
    transmit radio frequency (RF) signals to the plurality of connectors; and
    receive RFID signals from the plurality of connectors.

3. The dialysis system of claim 1, wherein the controller is further configured to detect that the first dialysate bag is empty based, at least in part, on the accessed information.

4. The dialysis system of claim 1, wherein the first connector includes a first portion and a second portion, and wherein at least one of the first portion or the second portion includes a radio frequency identifier (RFID) device that is operational when the first portion is mated with the second portion and is not operational when the first portion is disconnected from the second portion.

5. The dialysis system of claim 4, wherein the second portion includes an RFID antenna, and wherein the first portion includes an RFID chip.

6. The dialysis system of claim 4, wherein the second portion includes an interconnect configured to route a signal from a first terminal to a second terminal, and wherein the first portion includes an RFID chip and an antenna, and wherein a signal interconnect from the RFID chip is connected to the first terminal and the second terminal is connected to the antenna when the first portion is mated to the second portion.

7. The dialysis system of claim 4, wherein the second portion includes a first memory that stores second information that identifies the first port,
wherein the first portion includes a second memory that stores first information that indicates the first formulation of the first dialysis bag, and
wherein the first portion further includes an RFID chip configured to encode the first and second information and to transmit the first and second information to the reader.

8. A method for operating a dialysis system, comprising:
wirelessly accessing, by a reader of the dialysis system, information from a plurality of connectors, wherein the plurality of connectors are attached to a plurality of fluid lines coupled to a plurality of dialysate bags, and wherein the plurality of connectors are fluidly coupled to a plurality of ports of a disposable cassette;
receiving, by a controller of the dialysis system, the accessed information from the reader, wherein the accessed information indicates a first formulation of a first dialysate bag of the plurality of dialysate bags and a second formulation of a second dialysate bag of the plurality of dialysate bags, wherein the first dialysate bag is fluidly coupled to a first port of the plurality of ports via a first connector of the plurality of connectors, and wherein the second dialysate bag is fluidly coupled to a second port of the plurality of ports via a second connector of the plurality of connectors; and
adjusting, by the controller, operation of at least one component of the dialysis system based on the accessed information;
wherein adjusting the operation of the at least one component of the dialysis system comprises:
determining that the first formulation of the first dialysate bag is different than the second formulation of the second dialysate bag based on the accessed information; and
mixing a first volume of the first formulation from the first dialysate bag with a second volume of the second formulation from the second dialysate bag to create a volume of mixed dialysate solution;
wherein the first connector includes a first tag of a plurality of tags, and the second connector includes a second tag of the plurality of tags;
wherein each tag of the plurality of tags comprises a chip, a memory, and an antenna. and wherein the memory of a respective tag of the plurality of tags includes multiple bits which specify a respective index of a plurality of indexes, wherein the respective index indicates a respective constituent-concentration-volume combination of a plurality of constituent-concentration-volume combinations, and wherein the respective constituent-concentration-volume combination indicates that a respective corresponding dialysate bag of the plurality of dialysate bags contains a respective volume of a respective formulation and that the respective formulation includes a respective constituent at a respective concentration.

9. The method of claim 8, wherein the reader is a near field communication (NFC) device, and wherein the method further comprises:
transmitting, by the reader, a-radio frequency (RF) signals to the plurality of connectors; and
receiving, by the reader, RFID signals from the plurality of connectors.

10. The method of claim 8, further comprising:
detecting, by the controller, that the first dialysis bag is empty based, at least in part, on the accessed information.

11. A non-transitory computer-readable medium having processor-executable instructions stored thereon for operating a dialysis system, wherein the processor-executable instructions, when executed, facilitate performance of the following:
wirelessly accessing, by a reader of the dialysis system, access information from a plurality of connectors, wherein the plurality of connectors are attached to a plurality of fluid lines coupled to a plurality of dialysate bags, and wherein the plurality of connectors are fluidly coupled to a plurality of ports of a disposable cassette;
receiving, by a controller of the dialysis system, the accessed information from the reader, wherein the accessed information indicates a first formulation of a first dialysate bag of the plurality of dialysate bags and a second formulation of a second dialysate bag of the plurality of dialysate bags, wherein the first dialysate bag is fluidly coupled to a first port of the plurality of ports via a first connector of the plurality of connectors, and wherein the second dialysate bag is fluidly coupled to a second port of the plurality of ports via a second connector of the plurality of connectors; and
adjusting, by the controller, operation of at least one component of the dialysis system based on the accessed information;
wherein adjusting the operation of the at least one component of the dialysis system comprises:
determining that the first formulation of the first dialysate bag is different than the second formulation of the second dialysate bag based on the accessed information; and
mixing a first volume of the first formulation from the first dialysate bag with a second volume of the second formulation from the second dialysate bag to create a volume of mixed dialysate solution;
wherein the first connector includes a first tag of a plurality of tags, and the second connector includes a second tag of the plurality of tags;
wherein each tag of the plurality of tags comprises a chip, a memory, and an antenna, and wherein the memory of a respective tag of the plurality of tags includes multiple bits which specify a respective index of a plurality of indexes, wherein the respective index indicates a respective constituent-concentration-volume combination of a plurality of constituent-concentration-volume combinations, and wherein the respective constituent-concentration-volume combination indicates that a respective corresponding dialysate bag of the plurality of dialysate bags contains a respective volume of a respective formulation and that the respective formulation includes a respective constituent at a respective concentration.

12. The non-transitory computer-readable medium of claim 11, wherein the reader is a near field communication (NFC) device, and wherein the processor-executable instructions, when executed, further facilitate performance of the following:
   transmitting, by the reader, radio frequency (RF) signals to the plurality of connectors; and
   receiving, by the reader, RFID signals from the plurality of connectors.

13. The non-transitory computer-readable medium of claim 11, wherein the processor-executable instructions, when executed, further facilitate performance of the following:
   detecting, by the controller, that the first dialysis bag is empty based, at least in part, on the accessed information.

* * * * *